US009043160B1

(12) United States Patent
Moorhead et al.

(10) Patent No.: US 9,043,160 B1
(45) Date of Patent: *May 26, 2015

(54) METHOD OF DETERMINING CLONOTYPES AND CLONOTYPE PROFILES

(75) Inventors: Martin Moorhead, San Mateo, CA (US); Malek Faham, Pacifica, CA (US); Thomas Willis, San Francisco, CA (US)

(73) Assignee: SEQUENTA, INC., South San Francisco, CA (US)

( * ) Notice: Subject to any disclaimer, the term of this patent is extended or adjusted under 35 U.S.C. 154(b) by 424 days.

This patent is subject to a terminal disclaimer.

(21) Appl. No.: 13/196,885

(22) Filed: Aug. 2, 2011

Related U.S. Application Data

(63) Continuation-in-part of application No. 13/100,389, filed on May 4, 2011, now Pat. No. 8,691,510, which is a continuation-in-part of application No. 12/615,263, filed on Nov. 9, 2009, now Pat. No. 8,236,503.

(60) Provisional application No. 61/446,822, filed on Feb. 25, 2011, provisional application No. 61/455,743, filed on Oct. 25, 2010.

(51) Int. Cl.
G06F 7/00 (2006.01)
G06F 19/14 (2011.01)

(52) U.S. Cl.
CPC ..................... G06F 19/14 (2013.01)

(58) Field of Classification Search
CPC .. C12Q 1/6869; C12Q 1/6827; C12Q 1/6881; C12Q 2537/165; G06F 19/24; G06F 12/1408; G06F 19/14; G06F 19/22; G06F 21/445; G06F 21/57; G06F 21/606; G06F 21/72; G06F 21/73; G06F 21/75
See application file for complete search history.

(56) References Cited

U.S. PATENT DOCUMENTS

| | | |
|---|---|---|
| 5,296,351 A | 3/1994 | Morley .................. 435/6 |
| 5,298,396 A | 3/1994 | Kotzin et al. |
| 5,336,598 A | 8/1994 | Kotzin et al. |
| 5,418,134 A | 5/1995 | Morley .................. 435/6 |
| 5,635,354 A | 6/1997 | Kourilsky et al. |
| 5,698,396 A | 12/1997 | Pfreundschuh |
| 5,776,708 A | 7/1998 | Kotzin et al. |
| 5,837,447 A | 11/1998 | Gorski .................. 435/6 |
| 6,087,096 A | 7/2000 | Dau .................. 435/6 |
| 6,090,592 A | 7/2000 | Adams et al. |
| 6,258,568 B1 | 7/2001 | Nyren |
| 6,416,948 B1 | 7/2002 | Pilarski et al. |
| 6,524,829 B1 | 2/2003 | Seeger |
| 6,596,492 B2 | 7/2003 | Avery et al. |
| 6,667,159 B1 | 12/2003 | Walt |
| 6,964,850 B2 | 11/2005 | Bevilacqua |
| 7,306,906 B2 | 12/2007 | Maruyama et al. |
| 7,375,211 B2 | 5/2008 | Kou .................. 536/24.33 |
| 7,691,994 B2 | 4/2010 | Brewer .................. 536/24.33 |
| 7,749,697 B2 | 7/2010 | Oleksiewicz et al. |
| 8,236,503 B2 | 8/2012 | Faham et al. |
| 8,283,294 B2 | 10/2012 | Kastrup et al. |
| 8,507,205 B2 | 8/2013 | Faham et al. |
| 8,628,927 B2 | 1/2014 | Faham et al. |
| 8,691,510 B2 | 4/2014 | Faham et al. |
| 8,748,103 B2 | 6/2014 | Faham et al. |
| 8,795,970 B2 | 8/2014 | Faham et al. |
| 2002/0076725 A1 | 6/2002 | Toyosaki-Maeda et al. |
| 2003/0096277 A1 | 5/2003 | Chen |
| 2003/0162197 A1 | 8/2003 | Morley et al. |
| 2004/0132050 A1 | 7/2004 | Monforte |
| 2004/0248172 A1 | 12/2004 | Samoszuk et al. |
| 2005/0064421 A1 | 3/2005 | Gehrmann .................. 435/6 |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |

(Continued)

FOREIGN PATENT DOCUMENTS

| | | |
|---|---|---|
| EP | 1544308 B1 | 6/2005 |
| EP | 1549764 B1 | 7/2005 |
| EP | 2364368 B1 | 1/2014 |
| JP | 2007-536939 A | 12/2007 |
| JP | 2008099588 A | 5/2008 |
| WO | WO 93/01838 A1 | 2/1993 |
| WO | WO 2005/059176 A1 | 6/1995 |
| WO | WO 95/28481 A1 | 10/1995 |

(Continued)

OTHER PUBLICATIONS

Andreasson et al. (Andreasson et al. 2006 J Mol Biol 362:212-227).*
Shendure et al (2008) "Next-generation DNA sequencing," Nature Biotechnology, 26(10): 1135-1145.
Stewart et al (1994) "Immunoglobulin V regions and the B cell," Blood, 83(7): 1717-1730.

(Continued)

Primary Examiner — Mary Zeman
(74) Attorney, Agent, or Firm — Wilson Sonsini Goodrich & Rosati

(57) ABSTRACT

The invention is directed to methods for determining clonotypes and clonotype profiles in assays for analyzing immune repertoires by high throughput nucleic acid sequencing of somatically recombined immune molecules. In one aspect, the invention comprises generating a clonotype profile from an individual by generating sequence reads from a sample of recombined immune molecules; forming from the sequence reads a sequence tree representing candidate clonotypes each having a frequency; coalescing with a highest frequency candidate clonotype any lesser frequency candidate clonotypes whenever such lesser frequency is below a predetermined value and whenever a sequence difference therebetween is below a predetermined value to form a clonotype. After such coalescence, the candidate clonotypes is removed from the sequence tree and the process is repeated. This approach permits rapid and efficient differentiation of candidate clonotypes with genuine sequence differences from those with experimental or measurement errors, such as sequencing errors.

45 Claims, 11 Drawing Sheets

(56) References Cited

U.S. PATENT DOCUMENTS

| | | | |
|---|---|---|---|
| 2006/0147925 A1 | 7/2006 | Morley et al. | |
| 2006/0234234 A1 | 10/2006 | Van Dongen | 435/6 |
| 2006/0259248 A1 | 11/2006 | Collette et al. | |
| 2007/0105105 A1 | 5/2007 | Clelland et al. | |
| 2007/0117134 A1 | 5/2007 | Kou | 536/24.33 |
| 2007/0160994 A1 | 7/2007 | Lim et al. | |
| 2007/0161001 A1 | 7/2007 | Leshkowitz | 435/6 |
| 2007/0238099 A1 | 10/2007 | Cohen et al. | |
| 2007/0286849 A1 | 12/2007 | Chaturvedi | |
| 2008/0050780 A1 | 2/2008 | Lee et al. | |
| 2008/0108509 A1 | 5/2008 | Haupl | 506/8 |
| 2008/0166704 A1 | 7/2008 | Marche | 435/6 |
| 2008/0166718 A1 | 7/2008 | Lim et al. | |
| 2008/0248484 A1 | 10/2008 | Bauer | |
| 2008/0274904 A1 | 11/2008 | Gormley et al. | |
| 2008/0280774 A1 | 11/2008 | Burczynski | 506/9 |
| 2008/0286777 A1 | 11/2008 | Candeias | 435/6 |
| 2009/0053184 A1 | 2/2009 | Morgan | 424/93.21 |
| 2009/0181859 A1 | 7/2009 | Muraguchi | |
| 2009/0197257 A1 | 8/2009 | Harris | |
| 2009/0226975 A1 | 9/2009 | Sabot et al. | |
| 2009/0253581 A1 | 10/2009 | Van Eijk et al. | |
| 2009/0280489 A1 | 11/2009 | Devinder | 435/6 |
| 2009/0298060 A1 | 12/2009 | Lal et al. | |
| 2010/0021896 A1 | 1/2010 | Han | 435/6 |
| 2010/0021984 A1 | 1/2010 | Edd | |
| 2010/0035764 A1 | 2/2010 | Chen | 506/9 |
| 2010/0040606 A1 | 2/2010 | Lantto et al. | |
| 2010/0042329 A1 | 2/2010 | Hood et al. | |
| 2010/0151471 A1 | 6/2010 | Faham et al. | |
| 2010/0173394 A1 | 7/2010 | Colston, Jr. | |
| 2010/0255471 A1 | 10/2010 | Clarke | |
| 2010/0285975 A1 | 11/2010 | Mathies | |
| 2010/0330571 A1 | 12/2010 | Robins | 435/6 |
| 2011/0003291 A1 | 1/2011 | Pasqual | 435/6 |
| 2011/0207134 A1 | 8/2011 | Faham et al. | |
| 2011/0207135 A1 | 8/2011 | Faham et al. | |
| 2011/0207617 A1 | 8/2011 | Faham et al. | |
| 2012/0135409 A1 | 5/2012 | Faham et al. | |
| 2012/0220466 A1 | 8/2012 | Fire et al. | |
| 2013/0005584 A1 | 1/2013 | Faham et al. | |
| 2013/0017957 A1 | 1/2013 | Faham et al. | |
| 2013/0065768 A1 | 3/2013 | Zheng et al. | |
| 2013/0136799 A1 | 5/2013 | Faham et al. | |
| 2013/0150252 A1 | 6/2013 | Faham et al. | |
| 2013/0196328 A1 | 8/2013 | Pepin et al. | |
| 2013/0202718 A1 | 8/2013 | Pepin et al. | |
| 2013/0236895 A1 | 9/2013 | Faham et al. | |
| 2013/0267427 A1 | 10/2013 | Faham et al. | |
| 2013/0302801 A1 | 11/2013 | Asbury et al. | |
| 2013/0324422 A1 | 12/2013 | Faham et al. | |
| 2013/0344066 A1 | 12/2013 | Faham et al. | |
| 2014/0127699 A1 | 5/2014 | Han | |
| 2014/0213463 A1 | 7/2014 | Robins et al. | |
| 2014/0234835 A1 | 8/2014 | Pepin et al. | |
| 2014/0235454 A1 | 8/2014 | Faham et al. | |
| 2014/0255929 A1 | 9/2014 | Zheng | |
| 2014/0255944 A1 | 9/2014 | Carlton et al. | |
| 2014/0256592 A1 | 9/2014 | Faham et al. | |
| 2014/0315725 A1 | 10/2014 | Faham et al. | |
| 2014/0336059 A1 | 11/2014 | Faham et al. | |
| 2014/0342360 A1 | 11/2014 | Faham et al. | |
| 2014/0342367 A1 | 11/2014 | Faham et al. | |

FOREIGN PATENT DOCUMENTS

| | | |
|---|---|---|
| WO | WO 97/18330 A1 | 5/1997 |
| WO | WO 97/46706 A1 | 12/1997 |
| WO | WO 98/01738 A1 | 1/1998 |
| WO | WO 03/044225 A2 | 5/2003 |
| WO | WO 03/059155 A2 | 7/2003 |
| WO | WO 2004/003820 A2 | 1/2004 |
| WO | WO 03/059155 A3 | 3/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/046098 A3 | 8/2004 |
| WO | WO 2004/096985 A2 | 11/2004 |
| WO | WO 2005/005651 A2 | 1/2005 |
| WO | WO 2005/042774 A2 | 5/2005 |
| WO | WO 2005/053603 A2 | 6/2005 |
| WO | WO 2005/084134 A2 | 9/2005 |
| WO | WO2006/076025 | 7/2006 |
| WO | WO 2006/110855 A2 | 10/2006 |
| WO | WO 2006/116155 A2 | 11/2006 |
| WO | WO2008/026927 | 3/2008 |
| WO | WO 2008/039694 A2 | 4/2008 |
| WO | WO2008/108803 | 9/2008 |
| WO | WO2008/147879 | 12/2008 |
| WO | WO 2009/015296 A1 | 1/2009 |
| WO | WO 2009/019657 A2 | 2/2009 |
| WO | WO 2009/021215 A1 | 2/2009 |
| WO | WO2009/045898 | 4/2009 |
| WO | WO 2009/070767 A2 | 6/2009 |
| WO | WO 2009/019657 A3 | 8/2009 |
| WO | WO 2009/108860 A2 | 9/2009 |
| WO | WO 2009/108866 A2 | 9/2009 |
| WO | WO 2009/070767 A3 | 10/2009 |
| WO | WO 2009/108866 A3 | 10/2009 |
| WO | WO2009/137255 | 11/2009 |
| WO | WO 2009/137832 A2 | 11/2009 |
| WO | WO 2009/145925 A1 | 12/2009 |
| WO | WO2009/151628 | 12/2009 |
| WO | WO 2009/158521 A2 | 12/2009 |
| WO | WO 2009/108860 A3 | 1/2010 |
| WO | WO 2010/011894 A1 | 1/2010 |
| WO | WO 2010/036352 A1 | 4/2010 |
| WO | WO 2009/158521 A3 | 5/2010 |
| WO | WO 2010/053587 A2 | 5/2010 |
| WO | WO2010/51416 | 12/2010 |
| WO | WO 2011/083296 A1 | 7/2011 |
| WO | WO 2011/106738 A2 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2011/106738 A3 | 12/2011 |
| WO | WO 2012/048340 A2 | 4/2012 |
| WO | WO 2012/061832 A1 | 5/2012 |
| WO | WO 2012/048340 A3 | 6/2012 |
| WO | WO 2013/036459 A2 | 3/2013 |
| WO | WO 2013/055595 A1 | 4/2013 |
| WO | WO 2013/066726 A1 | 5/2013 |
| WO | WO 2013/085855 A1 | 6/2013 |
| WO | WO 2013/086462 A1 | 6/2013 |
| WO | WO 2013/090390 A1 | 6/2013 |
| WO | WO 2013/090469 A1 | 6/2013 |
| WO | WO 2013/096480 A2 | 6/2013 |
| WO | WO 2013/134162 A2 | 9/2013 |
| WO | WO 2013/134302 A1 | 9/2013 |
| WO | PCT/US2013/065493 | 10/2013 |
| WO | PCT/US2013/065509 | 10/2013 |
| WO | PCT/US2013/065757 | 10/2013 |
| WO | WO 2013/155119 A1 | 10/2013 |
| WO | WO 2013/158936 A1 | 10/2013 |
| WO | WO 2013/181428 A2 | 12/2013 |
| WO | WO 2013/188471 A2 | 12/2013 |
| WO | WO 2014/018460 A1 | 1/2014 |
| WO | PCT/US2014/017416 | 2/2014 |
| WO | WO 2014/026031 A1 | 2/2014 |
| WO | PCT/US2014/044971 | 6/2014 |
| WO | PCT/US2014/047909 | 7/2014 |
| WO | WO 2014/130685 A1 | 8/2014 |
| WO | PCT/US2014/061260 | 10/2014 |

OTHER PUBLICATIONS

Weinstein et al (2009) "High-throughput sequencing of the zebrafish antibody repertoire," Science, 324: 807-810, including supporting online materials.
U.S. Appl. No. 14/363,276, filed Jun. 5, 2014, Faham et al.
U.S. Appl. No. 14/363,956, filed Jun. 9, 2014, Faham et al.
U.S. Appl. No. 14/364,961, filed Jun. 12, 2014, Faham et al.

(56) References Cited

OTHER PUBLICATIONS

U.S. Appl. No. 14/366,840, filed Jun. 19, 2014, Faham.
U.S. Appl. No. 14/383,101, filed Sep. 4, 2014, Faham et al.
U.S. Appl. No. 14/383,102, filed Sep. 4, 2014, Faham.
Nie, et al. Optical detection of single molecules. Annu Rev Biophys Biomol Struct. 1997;26:567-96.
Office action dated Aug. 26, 2014 for U.S. Appl. No. 14/075,075.
Drossman, et al. High-speed separations of DNA sequencing reactions by capillary electrophoresis. Anal Chem. May 1, 1990;62(9):900-3.
Office action dated Nov. 20, 2014 for U.S. Appl. No. 13/214,111.
U.S. Appl. No. 61/112,693, filed Nov. 7, 2008, Faham et al.
Abath, et al. Single-tube nested PCR using immobilized internal primers. Biotechniques. Dec. 2002;33(6):1210-2, 1214.
Altin, et al. The role of CD45 and CD45-associated molecules in T cell activation. Immunol Cell Biol. Oct. 1997;75(5):430-45.
Arnaout. Specificity and overlap in gene segment-defined antibody repertoires. C Genomics. Oct. 28, 2005;6:148.
Damle, et al. B-cell chronic lymphocytic leukemia cells express a surface membrane phenotype of activated, antigen-experienced B lymphocytes. Blood. Jun. 1, 2002;99(11):4087-93.
De Bona, et al. Optimal spliced alignments of short sequence reads. Bioinformatics. Aug. 15, 2008;24(16):i174-80. doi: 10.1093/bioinformatics/btn300.
Diluvio, et al. Identical TCR beta-chain rearrangements in streptococcal angina and skin lesions of patients with psoriasis vulgaris. J Immunol. Jun. 1, 2006;176(11):7104-11.
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Droege, et al. The Genome Sequencer FLX System—longer reads, more applications, straight forward bioinformatics and more complete data sets. J Biotechnol. Aug. 31, 2008;136(1-2):3-10. doi: 10.1016/j.jbiotec.2008.03.021. Epub Jun. 21, 2008.
Eisenstein. Personalized, sequencing-based immune profiling spurs startups. Nat Biotechnol. Mar. 2013;31(3):184-6. doi: 10.1038/nbt0313-184b.
Erlich, et al. Alta-Cyclic: a self-optimizing base caller for next-generation sequencing. Nat Methods. Aug. 2008;5(8):679-82. doi: 10.1038/nmeth.1230. Epub Jul. 6, 2008.
European opposition dated Oct. 14, 2014 for EP Application No. 09764971.1. Reference# 547-7.
European opposition dated Oct. 14, 2014 for EP Application No. 09764971.1. Reference# BRO-O001EP.
European opposition dated Oct. 15, 2014 for EP Application No. 09764971.1. (in French only).
Furmanski, et al. Public T cell receptor beta-chains are not advantaged during positive selection. J Immunol. Jan. 15, 2008;180(2):1029-39.
GIGA—Roche 454 FLX technology how it works. Fiche technique du Centre Interdisciplinaire de Genoproteomique Appliquee (Universite de Liege, Belgique). Accessed Oct. 15, 2014.
Gomes, et al. Single-tube nested PCR using immobilized internal primers for the identification of dengue virus serotypes. J Virol Methods. Oct. 2007;145(1):76-9. Epub Jun. 15, 2007.
Gupta. Single-molecule DNA sequencing technologies for future genomics research. Trends Biotechnol. Nov. 2008;26(11):602-11. doi: 10.1016/j.tibtech.2008.07.003. Epub Aug. 21, 2008.
Heger. Roche's 454 Eyes Immune Repertoire Sequencing as Key Application for Long-Read Platform. Feb. 2, 2010. http://www.genomeweb.com/print/932624.
IlluminA Systems & Software, Technology Spotlight, DNA Sequencing with Solexa® Technology, Illumina, Inc., Pub. No. 770-2007-002, 2007.
Jurkat, Clone 6-1 (ATCC TIB-152) Webpage retrievable from the ATCC under http://www.lgcstandards-atcc.org/Products/A11MB-152.aspx#characteristics. Accessed Oct. 14, 2014.
Lin, et al. Multiplex genotype determination at a large number of gene loci. Proc Natl Acad Sci U S A. Mar. 19, 1996;93(6):2582-7.
Lowe, et al. A computer program for selection of oligonucleotide primers for polymerase chain reactions. Nucleic Acids Res. Apr. 11, 1990;18(7):1757-61.
Mardis. Next-generation DNA sequencing methods. Annu Rev Genomics Hum Genet. 2008;9:387-402. doi: 10.1146/annurev.genom.9.081307.164359.
Miceli, et al. The roles of CD4 and CD8 in T cell activation. Semin Immunol. May 1991;3(3):133-41. Abstract only.
Office action dated May 2, 2011 for U.S. Appl. No. 12/425,310.
Office action dated May 8, 2014 for U.S. Appl. No. 12/425,310.
Office action dated Aug. 6, 2010 for U.S. Appl. No. 12/425,310.
Quick. SOLiD System—a next-gen DNA sequencing platform announced, Gizmag online magazine, http://www.mizmag.com/go/8248, pp. 1-5, Oct. 2007.
Robins. Immunosequencing: applications of immune repertoire deep sequencing. Curr Opin Immunol. Oct. 2013;25(5):646-52. doi: 10.1016/j.coi.2013.09.017. Epub Oct. 16, 2013.
Sequenta and iRepertoire Join Forces on Blood Cancer Testing. BusinessWire. Aug. 8, 2013. http://www.businesswire.com/news/home/20130808005363/en/Sequenta-iRepertoire-Join-Forces-Blo...#.VGTT9Wd0yUk.
Shendure, et al. Advanced sequencing technologies: methods and goals. Nat Rev Genet. May 2004;5(5):335-44.
Shendure, et al. Next-generation DNA sequencing. Nat Biotechnol. Oct. 2008;26(10):1135-45. doi: 10.1038/nbt1486.
Stanley. Essentials of Immunology & Serology, Delmar, Thomson Learning, Chapter 7, T cells, p. 95, 2002.
Striebich, et al. Selective accumulation of related CD4+ T cell clones in the synovial fluid of patients with rheumatoid arthritis. J Immunol Oct. 15, 1998;161(8):4428-36.
Supplemental material of Weinstein, et al. High-throughput sequencing of the zebrafish antibody repertoire. Science. May 8, 2009;324(5928):807-10. doi: 10.1126/science.1170020. www.sciencemag.org/cgi/content/full/324/5928/807/DC1.
Vanderborght, et al. Dynamic T cell receptor clonotype changes in synovial tissue of patients with early rheumatoid arthritis: effects of treatment with cyclosporin A (Neoral). J Rheumatol. Mar. 2002;29(3):416-26.
Wang, et al. HIV integration site selection: analysis by massively parallel pyrosequencing reveals association with epigenetic modifications. Genome Res. Aug. 2007;17(8):1186-94. Epub Jun. 1, 2007.
Notice of allowance dated Sep. 12, 2014 for U.S. Appl. No. 13/214,111.
Office action dated Oct. 8, 2014 for U.S. Appl. No. 13/459,701.
U.S. Appl. No. 14/317,087, filed Jun. 27, 2014, Asbury et al.
U.S. Appl. No. 14/329,873, filed Jul. 11, 2014, Faham et al.
U.S. Appl. No. 14/350,516, filed Apr. 8, 2014, Faham et al.
U.S. Appl. No. 14/350,785, filed Apr. 9, 2014, Faham et al.
Kou, et al. T-Cell receptor Vbeta repertoire CDR3 length diversity differs within CD45RA and CD45RO T-cell subsets in healthy and human immunodeficiency virus-infected children. Clin Diagn Lab Immunol. Nov. 2000;7(6):953-9.
Miqeu, et al. Statistical analysis of CDR3 length distributions for the assessment of T and B cell repertoire biases. Mol Immunol. Feb. 2007;44(6):1057-64. Epub Aug. 2006.
Kita, et al. T cell receptor clonotypes in skin lesions from patients with systemic lupus erythematosus. J Invest Dermatol. Jan. 1998;110(1):41-6.
European search report and opinion dated Mar. 13, 2014 for EP Application No. 13195379.6.
European search report and opinion dated Jul. 26, 2013 for EP Application No. 11777704.5.
Greenberg, et al. Profile of immunoglobulin heavy chain variable gene repertoires and highly selective detection of malignant clonotypes in acute lymphoblastic leukemia. J Leukoc Biol. Jun. 1995;57(6):856-64.
International preliminary report on patentability dated May 19, 2011 for PCT/US2009/006053.
Thor Straten, et al. T-cell clonotypes in cancer.J Transl Med. Apr. 8, 2004;2(1):11.
Arnaout et al, "High-resolution description of antibody heavy-chain repertoires in humans," PLos ONE, 6(8): e22365 (2011).

(56) References Cited

OTHER PUBLICATIONS

Baldauf, "Phylogeny for the faint of heart: a tutorial," Trends in Genetics, 19(6): 345-351 (2003).
Bravo et al, "Model-based quality assessment and base-calling for second-generation sequencing data," Biometrics, 66(3): 665-674 (2010).
Brockman et al, "Quality scores and SNP detection in sequencing-by-synthesis systems," Genome Research, 18: 763-770 (2008).
Felsenstein, et al. Evolutionary Trees from DNA Sequences: A Maximum Likelihood Approach. J Mol Evol (1981) 17:368-376.
Flicek et al, "Sense from sequence reads: methods for alignment and assembly," Nature Methods Supplement, 6(11s): S6-S12 (2009).
Holder, et al. Phylogeny estimation: traditional and bayesian approaches. Nat Rev Genet. Apr. 2003;4(4):275-84.
Kircher et al, "Improved base calling for the Illumina Genome Analyzer using machine learning strategies," Genome Biology, 10: R83 (2009).
Lazareva-Ulitsky et al, "On the quality of tree-based protein classification," Bioinformatics, 21(9): 1876-1890 (2005).
Li et al, "Mapping short DNA sequencing reads and calling variants using mapping quality scores," Genome Research, 18: 1851-1858 (2008).
Office action dated Oct. 7, 2013 for U.S. Appl. No. 13/459,701.
Office action dated Oct. 16, 2013 for U.S. Appl. No. 13/487,980.
Office action dated Nov. 6, 2013 for U.S. Appl. No. 13/468,323.
Paszkiewicz et al, "De novo assembly of short sequence reads," Briefings in Bioinformatics, 11(5): 457-472 (2010).
Smith et al, "Using quality scores and longer reads improves accuracy of Solexa read mapping," BMC Bioinformatics, 9: 128 (2008).
Whiteford et al, "Swift: primary data analysis for the Illumina Solexa sequencing platform," Bioinformatics, 25(17): 2194-2199 (2009).
U.S. Appl. No. 13/905,406, filed May 30, 2013, Faham et al.
U.S. Appl. No. 13/908,813, filed Jun. 3, 2013, Faham et al.
Chen, A novel approach for the analysis of T-cell reconstitution by using a T-cell receptor beta-based oligonucleotide microarray in hematopoietic stem cell transplantation. Exp Hematol. May 2007;35(5):831-41.
Office action dated Jun. 6, 2013 for U.S. Appl. No. 13/100,365.
Office action dated Jun. 6, 2013 for U.S. Appl. No. 13/100,389.
Office action dated Jun. 20, 2013 for U.S. Appl. No. 13/214,111.
Office action dated Jul. 5, 2013 for U.S. Appl. No. 13/763,978.
U.S. Appl. No. 13/861,941, filed Apr. 12, 2013, Pepin et al.
Wu, et al. High-throughput sequencing detects minimal residual disease in acute T lymphoblastic leukemia. Sci Transl Med. May 16, 2012;4(134):134ra63. doi: 10.1126/scitranslmed.3003656.
Office action dated Apr. 22, 2013 for U.S. Appl. No. 13/214,111.
Arstila et al, "A direct estimate of the human $\alpha\beta$ T cell receptor diversity," Science, 286: 958-961 (1999).
Batzoglou et al, "The many faces of sequence alignment," Briefings in Bioinformatics, 6: 6-22 (2005).
Boria et al, "Primer sets for cloning the human repertoire of T cell receptor variable regions," BMC Immunology, 9: 50 (2008).
Boyd et al, "Measurement and clinical monitoring of human lymphocyte clonality by massively parallel VDJ pyrosequencing," Science Transl. Med. 1(12): 12ra23 (2009).
Campbell et al, "Subclonal phylogenic structures in cancer revealed by ultra-deep sequencing," Proc. Natl. Acad. Sci., 105(35): 13081-13086 (2008).
Dohm et al, "Substantial biases in ultra-short read data sets from high-throughput DNA sequencing," Nucleic Acids Research, 36: e105 (2008).
Du et al, "TCR spectrotyping revealed T lymphocytes associated with graft-versus-host disease after allogenic hematopoietic stem cell transplantation," Leukemia & Lymphoma, 48(8): 1618-1627 (2007).
Freeman et al, "Profiling the T-cell receptor beta-chain repertoire by massively parallel sequencing," Genome Research, 19(10): 1817-1824 (2009).
Han, et al. Immunorepertoire analysis by multiplex PCR amplification and high throughput sequencing. Abstract. The 96 Annual Meeting of The Americ.an Association of Immunologists, Seattle, Washington, May 8-12, 2009. Available at http://jimmunol.org//cgi/contentimeeting_abstractII82/1_MeetingAbstracts/42.6?sid=257929fl-97a9-4330-8e96-1750aa240e69. Accesssed 11/24/2010.
Holt, "Q & A: BC Cancer Agency's Robert Holt on sequencing the immune repertoire," GenomeWeb (www.genomeweb.com) (Jun. 30, 2009).
International Search Report dated Jun. 15, 2010 for PCT/US2009/006053.
Li et al, "Sequence analysis of clonal immunoglobulin and T-cell receptor gene rearrangements in childred with acute lymphoblastic leukemia at diagnosis and at relapse: implications for pathogenesis and for the clinical utility of PCR-based methods of minimal residual disease detection," Blood, 102: 4520-4526 (2003).
Packer et al, "Optimized clonotypic analysis of T-cell receptor repertoire in immune reconstitution," Experimental Hematology, 35: 516-521 (2007).
Pop, et al. Bioinformaticschallenges of new sequencing technology. Trends Genet. Mar. 2008;24(3): 142-9.
Reinartz, et al, "Massively parallel signature sequencing (MPSS) as a tool for in-depth quantitative gene expression profiling in all organisms," Briefings in Functional Genomics and Proteomics, 1(1): 95-104 (Feb. 2002).
Robins et al, "Comprehensive assessment of T-cell receptor $\beta$ chain diversity in $\alpha\beta$ T cells," Blood, 114(19): 4099-4107 (2009).
Rougemont et al, "Probabilistic base calling of Solexa sequencing data," BMC Bioinformatics, 9: 431 (2008).
Wang, et al. High throughput sequencing reveals a complex pattern of dynamic interrelationships among human T cell subsets. Proc. Natl Acad Sci USA. Jan. 26, 2010; 107(4): 1518-1523.
Weinstein et al, "High throughput sequencing of the zebrafish antibody repertoire," Science, 324; 807-810 (2009).
Zhou et al, "High throughput analysis of TCR-$\beta$ rearrangement and gene expression in single cells," Laboratory Investigation, 86: 314-321 (2006).
U.S. Appl. No. 13/174,086, filed Jun. 30, 2011, Faham et al.
U.S. Appl. No. 61/045,586, filed Apr. 16, 2008, Han et al.
Cronn, et al. Multiplex sequencing of plant chloroplast genomes using Solexa sequencing-by-synthesis technology. Nucleic Acids Res. Nov. 2008;36(19):e122.
Curran et al., "Nucleotide sequencing of psoriatic arthritis tissue before and during methotrexate administration reveals a complex inflammatory T cell infiltrate with very few clones exhibiting features that suggest they drive the inflammatory process by recognizing autoantigens," J Immunol 172:1935-1944 (2004).
Deng et al., "Gene profiling involved in immature CD4+ T lymphocyte responsible for systemic lupus erythematosus," Molecular Immunology 43:1497-1507 (2006).
Fritz et al., "Alterations in the spinal cord T cell repertoire during relapsing experimental autoimmune encephalomyelitis," J Immunol 164:6662-6668 (2000).
Garcia-Castello, et al. Detection of clonal immunoglobulin and T-cell receptor gene recombination in hematological malignancies: monitoring minimal residual disease. Cardiovascular & Haematological Disorders-Drug Targets. 2009; 9:124-135.
Gonzalez, et al. Incomplete DJH rearrangements as a novel tumar target for minimal residual disease quantitation in multiple myeloma using real-time PCR. Leukemia. 2003; 17:1051-1057.
Gonzalez, et al. Incomplete DJH rearrangements of the IgH gene are frequent in multiple myeloma patients: immunobioligcal characteristics and clinical applications. Leukemia. 2003; 17:1398-1403.
Heger, M. Studies Highlight Challenges of Immune Repertoire Sequencing's Clinical Applicability. Available at http://www.genomeweb.com/sequencing/studies-highlight-challenges-immune-repertoire-sequencings-clinical-applicabilit?hq_e=el&hq_m=966798&hq_1=10&hq_v=2357e2f0b3. Accessed Apr. 6, 2011.
Ishii et al., "Isolation and expression profiling of genes upregulated in the peripheral blood cells of systemic lupus erythematosus patients," DNA Research 12:429-439 (2005).
Jacobi et al., "Activated memory B cell subsets correlate with disease activity in systemic lupus erythematosus: delineation by expression of CD27, IgD, and CD95," Arthritis & Rheumatism 58(6):1762-1773 (2008).

(56) References Cited

OTHER PUBLICATIONS

Jacobi et al., "Correlation between circulating CD27high plasma cells and disease activity in patients with systemic lupus erythematosus," Arthritis & Rheumatism 48(5):1332-1342 (2003).
Kato et al., "Analysis of accumulated T cell clonotypes in patients with systemic lupus erythematosus," Arthritis & Rheumatism 43(12):2712-2721 (2000).
Kneba, et al. Analysis of rearranged T-cell receptor beta-chain genes by polymerase chain reaction (PCR0 DNA sequencing and automated high resolution PCR fragment analysis. Blood. 1995; 86:3930-3937.
Laplaud et al., "Blood T-cell receptor β chain transcriptome in multiple sclerosis. Characterization of the T cells with altered CDR3 length distribution," Brain 127:981-995 (2004).
Laplaud et al., "Serial blood T cell repertoire alterations in multiple sclerosis patients; correlation with clinical and MRI parameters," J Neroimmunol 177:151-160 (2006).
Luo et al., "Analysis of the interindividual conservation of T cell receptor α- and β-chain variable regions gene in the peripheral blood of patients with systemic lupus erythematosus," Clin Exp Immunol 154:316-324 (2008).
Mato et al., "Correlation of clonal T cell expansion with disease activity in systemic lupus erythematosus," Int Immunol 9(4):547-554 (1997).
Matsumoto et al., "CDR3 spectratyping analysis of the TCR repertoire in myasthenia gravis," J Immunol 176:5100-5107 (2006).
Matsumoto et al., "Complementarity-determining region 3 spectratyping analysis of the TCR repertoire in multiple sclerosis," J Immunol 170:4846-4853 (2003).
Menezes et al., "A public T cell clonotype within a heterogeneous autoreactive repertoire is dominant in driving EAE," J Clin Invest 117(8):2176-2185 (2007).
Michalek, et al. Detection and long-term in vivo monitoring of individual tumor-specific T cell clones in patients with metastatic melanoma. J Immunol. Jun. 1, 2007;178(11):6789-95.
Muraro et al., "Molecular tracking of antigen-specific T cell clones in neurological immune-mediated disorders," Brain 126:20-31 (2003).
Notification of Grant dated Jul. 26, 2011 for patent serial No. GB 2467704.
Ogle, et al. Direst measurement of lymphocyte receptor diversity. Nucleic Acids. Research. 2003; 31(22):e139.
Okajima et al., "Analysis of T cell receptor Vβ diversity in peripheral CD4+ and CD8+ T lymphocytes in patients with autoimmune thyroid diseases," Clin Exp Immunol 155:166-172 (2008).
Risitano et al., "In-vivo dominant immune responses in aplastic anaemia: molecular tracking of putatively pathogenetic T-cell clones by TCR β-CDR3 sequencing," Lancet 364:355-364 (2004).
Schwab et al., "CD8+ T-cell clones dominate brain infiltrates in Rasmussen encephalitis and persist in the periphery," Brain 132:1236-1246 (2009).
Shen, et al. Comparing platforms for C. elegans mutant identification using high-throughput whole-genome sequencing. PLoS One. 2008;3(12):e4012.
Skulina et al., "Multiple sclerosis: brain-infiltrating CD8+ T cells persist as clonal expansions in the cerebrospinal fluid and blood," PNAS 101(8):2428-2433 (2004).
Sumida et al., "T cell receptor repertoire of infiltrating T cells in lips of Sjögren's syndrome patients," J Clin Invest 89:681-685 (1992).
Sumida et al., "T cell receptor Vα repertoire of infiltrating T cells in labial salivary glands from patients with Sjögren's syndrome," J Rheumatol 21: 1655-1661 (1994).
Tackenberg et al., "Clonal expansions of CD4+ β helper T cells in autoimmune myasthenia gravis," Eur J Immunol 37:849-863 (2007).
UK Combined Search Report and Office action dated May 26, 2011 for UK application No. GB1105068.9.
UK Search Report dated Jul. 6, 2010 for UK application No. GB1009641.0.
Umibe et al., "Clonal expansion of T cells infiltrating in the airways of non-atopic asthmatics," Clin Exp Immunol 119:390-397 (2000).

Warren et al., "Profiling model T-cell metagenomes with short reads," Bioinformatics 25(4):458-464 (2009).
Warren, et al. Exhaustive T-cell repertoire sequencing of human peripheral blood samples reveals signatures of antigen selection and a directly measured repertoire size of at least 1 million clonotypes. Genome Res. Feb. 24, 2011. [Epub ahead of print].
Wlodarski, et al. Molecular strategies for detection and quantitation of the clonal cytotoxic T-cell responses in aplastic anemia and myelodysplastic syndrome. Blood. 2006; 108:2632-2641.
Wlodarski, et al. Pathologic clonal cytotoxic T-cell responses: nonrandom nature of the T-cell-receptor restriction in large granular lymphocyte leukemia. Blood. 2005; 106:2769-2779.
Yin et al., "Antiretroviral therapy restores diversity in the T-cell receptor Vβ repertoire of CD4 T-cell subpopulations among human immunodeficiency virus type 1-infected children and adolescents," Clin Vac Immunol 16(9):1293-1301 (2009).
Brehm-Stecher, et al. Single-cell microbiology: tools, technologies, and applications. Microbiology and molecular biology reviews. 2004; 68(3):538-559.
Davis, et al. Staining of cell surface human CD4 with 2-F-pyrimidine-containing RNA amptamers for flow cytometry. Nucleic Acids Research. 1998; 26(17):3915-3924.
Edd, et al. Controlled encapsulation of single cells into monodisperse picoliter drops. Lap Chip. 2008; 8(8):1262-1264.
Giuggio, et al. Evolution of the intrahepatic T cell repertoire during chronic hepataitis C virus infection. Viral Immunol. 2005;18(1):179-89.
Jena, et al. Amplification of genes, single transcripts and cDNA libraries from one cell and direct sequence analysis of amplified products derived from one molecule. J. Immunol. Methods. 1996; 190:199-213.
Kim, et al an efficient and reliable DNA extraction method for preimplantation genetic diagnosis: a comparison of allele drop out and amplification rates using different single cell iysis methods. Fertility and Sterility. 2009; 92: 814-818.
Kobari, et al. T cells accumulating in the inflamed joints of a spontaneous murine model of rheumatoid arthritis become restricted to common clonotypes during disease progression. Int Immunol. Jan. 2004;16(1):131-8.
Li, et al. An improved one-tube RT-PCR protocol for analyzing single-cell gene expression in individual mammalian cells. Anal. Bioanal. Chem. 2010; 397: 1853-1859.
Novak, et al. Single-cell multiplex gene detection and sequencing with microfluidically generated agarose emulsions. Angewandte Chernie. 2011; 50: 390-395, with supplemental material.
Ray, et at. Single cell multiplex PCR amplification of five dystrophin gene exons combined with gender determination. Molecular Human Reproduction. 2001; 7(5): 489-494.
Tajiri, et al. Cell-microarray analysis of antigen-specific B-cells: single cell analysis of antigen receptor expression and specificity. Cytometry Part A. 2007; 71A: 961-967.
Thornhill, et al. A comparison of different lysis buffers to assess allele dropout from single cells for preimplantation genetic diagnosis. Prenatal Diagnosis. 2001; 21: 490-497.
Tokimitsu, et al. Single lymphocyte analysis with a microwell array chip. Cytometry. 2007; Part A, 71A: 1003-1010.
UK Search Report dated May 25, 2011 for UK application No. GB1009641.0.
Wells, et al. Strategies for preimplantation genetic diagnosis of single gene disorders by DNA amplification. Prenatal Diagnosis. 1998; 18: 1389-1401.
Wetmur, et al. An emulsion polymerase chain reaction-based method for molecular haplotyping. Methods in Molecular Biology. 1996; 410: 351-361.
Wetmur, et al. Linking emulsion PCR haplotype analysis. chapter 11, in Park (editor), PCR Protocols, Methods En Molecular Biology. 2011; 687: 165-175.
Wetmur, et al. Molecular haplotyping by linking emulsion PCR: analysis of paraoxonase 1 haplotypes and phenotypes. Nucleic Acids Research. 2005; 33(8):2615-2619.
Yon, et al. Precise gene fusion by PCR. Nucleic Acids Research. 1989; 17(12):4895.

(56) References Cited

OTHER PUBLICATIONS

Zeng, et al. High-performance single cell genetic analysis using microfluidic emulsion generator arrays. Anal. Chem. 2010; 82:3183-3190.
U.S. Appl. No. 13/487,980, filed Jun. 4, 2012, Faham et al.
U.S. Appl. No. 13/214,111, filed Aug. 19, 2011, Faham et al.
U.S. Appl. No. 13/369,031, filed Feb. 8, 2012, Faham et al.
Choi, et al. Clonal evolution in B-lineage acute lymphoblastic leukemia by contemporaneous VH-VH gene replacements and VH-DJH gene rearrangements. Blood. Mar. 15, 1996;87(6):2506-12.
Costabile, et al. Molecular approaches in the diagnosis of primary immunodeficiency diseases. Hum Mutat. Dec. 2006;27(12):1163-73.
International search report and written opinion dated Sep. 22, 2011 for PCT Application No. US11/000791.
International search report and written opinion dated Oct. 19, 2011 for PCT Application No. US11/000792.
Kim, et al. Polony multiplex analysis of gene expression (PMAGE) in mouse hypertrophic cardiomyopathy. Science. Jun. 8, 2007;316(5830):1481-4.
Margulies, et al. Genome sequencing in microfabricated high-density picolitre reactors. Nature. Sep. 15, 2005;437(7057):376-80. Epub Jul. 31, 2005.
Nardi, et al. Quantitative monitoring by polymerase colony assay of known mutations resistant to ABL kinase inhibitors. Oncogene. Jan. 31, 2008;27(6):775-82. Epub Aug. 6, 2007, 1-8.
UK office action dated May 25, 2011 for UK application No. GB1009641.0.
UK office action dated Oct. 20, 2010 for UK application No. GB1009641.0.
UK Search Report and office action dated Jan. 12, 2012 for UK application No. GB1120209.0.
UK Search Report and office action dated Jul. 7, 2010 for UK application No. GB1009641.0.
Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. Dec. 2003;17(12):2257-317.
U.S. Appl. No. 13/459,701, filed Apr. 30, 2012, Faham et al.
U.S. Appl. No. 13/468,323, filed May 10, 2012, Faham et al.
European office action dated Mar. 28, 2012 for EP Application No. 09764927.1.
Illumina. Data Sheet: Sequencing. Genomic Sequencing. Pub. No. 770.2008-016 Copyright 2010. Reference states: "Current as of Jan. 30, 2009".
Office action dated May 9, 2012 for U.S. Appl. No. 13/100,395.
Office action dated Sep. 15, 2011 for U.S. Appl. No. 12/615,263.
Bene, et al. How and why minimal residual disease studies are necessary in leukemia: a review from WP10 and WP12 of the European LeukaemiaNet. Haematologica. Aug. 2009;94(8):1135-50. Epub Jul. 7, 2009.
Benichou, et al. Rep-Seq: uncovering the immunological repertoire through next-generation sequencing. Immunology. Mar. 2012;135(3):183-91. doi: 10.1111/j.1365-2567.2011.03527.x.
Boyd, et al. Individual variation in the germline Ig gene repertoire inferred from variable region gene rearrangements. J Immunol Jun. 15, 2010;184(12):6986-92. Epub May 21, 2010.
Brisco, et al. Determining the repertoire of IGH gene rearrangements to develop molecular markers for minimal residual disease in B-lineage acute lymphoblastic leukemia. J Mol Diagn. May 2009;11(3):194-200. Epub Mar. 26, 2009.
Bruggemann, et al. Clinical significance of minimal residual disease quantification in adult patients with standard-risk acute lymphoblastic leukemia. Blood. Feb. 1, 2006;107(3):1116-23. Epub Sep. 29, 2005.
Campana. Minimal residual disease in acute lymphoblastic leukemia. Semin Hematol. Jan. 2009;46(1):100-6.
Choi, et al. Relapse in children with acute lymphoblastic leukemia involving selection of a preexisting drug-resistant subclone. Blood. Jul. 15, 2007;110(2):632-9. Epub Mar. 19, 2007.
Currier, et al. Spectratype/immunoscope analysis of the expressed TCR repertoire. Current Protocols in Immunology. 2000; Supplement 38:10.28.1-10.28.24.
Gorski, et al. Circulating T cell repertoire complexity in normal individuals and bone marrow recipients analyzed by CDR3 size spectratyping. Correlation with immune status. J Immunol May 15, 1994;152(10):5109-19.
Langerak, et al. Polymerase chain reaction-based clonality testing in tissue samples with reactive lymphoproliferations: usefulness and pitfalls. A report of the BIOMED-2 Concerted Action BMH4-CT98-3936. Leukemia. Feb. 2007;21(2):222-9. Epub Dec. 14, 2007.
Li, et al. Utilization of Ig heavy chain variable, diversity, and joining gene segments in children with B-lineage acute lymphoblastic leukemia: implications for the mechanisms of VDJ recombination and for pathogenesis. Blood. Jun. 15, 2004;103(12):4602-9. Epub Mar. 9, 2004.
Logan, et al. High-throughput VDJ sequencing for quantification of minimal residual disease in chronic lymphocytic leukemia and immune reconstitution assessment. Proc Natl Acad Sci U S A. Dec. 27, 2011;108(52):21194-9. Epub Dec. 12, 2011.
Lovisa, et al. IGH and IGK gene rearrangements as PCR targets for pediatric Burkitt's lymphoma and mature B-ALL MRD analysis. Lab Invest. Oct. 2009;89(10):1182-6. Epub Aug. 10, 2009.
Meleshko, et al. Rearrangements of IgH, TCRD and TCRG genes as clonality marker of childhood acute lymphoblastic leukemia. Exp Oncol. Dec. 2005;27(4):319-24.
Moss, et al. The human T cell reeptor in health and disease. Annu. Rev. Immunol. 1992; 10:71-96.
Neale, et al. Comparative analysis of flow cytometry and polymerase chain reaction for the detection of minimal residual disease in childhood acute lymphoblastic leukemia. Leukemia. May 2004;18(5):934-8.
Nguyen, et al. Identification of errors introduced during high throughput sequencing of the T cell receptor repertoire. BMC Genomics. Feb. 11, 2011;12:106.
Panzer-Grumayer, et al. Immunogenotype changes prevail in relapses of young children with TEL-AML1-positive acute lymphoblastic leukemia and derive mainly from clonal selection. Clin Cancer Res. Nov. 1, 2005;11(21):7720-7.
Reddy, et al. Systems analysis of adaptive immunity by utilization of high-throughput technologies. Curr Opin Biotechnol. Aug. 2011;22(4):584-9. Epub May 12, 2011.
Robins, et al. Ultra-sensitive detection of rare T cell clones. Immunol Methods. Jan. 31, 2012;375(1-2):14-9. Epub Sep. 10, 2011.
Sramkova, et al. Detectable minimal residual disease before allogeneic hematopoietic stem cell transplantation predicts extremely poor prognosis in children with acute lymphoblastic leukemia. Pediatr Blood Cancer. Jan. 2007;48(1):93-100.
Zaliova, et al. Quantification of fusion transcript reveals a subgroup with distinct biological properties and predicts relapse in BCR/ABL-positive ALL: implications for residual disease monitoring. Leukemia. May 2009;23(5):944-51. Epub Jan. 22, 2009.
Bonarius, et al. Monitoring the T-Cell Receptor Repertoire at Single-Clone Resolution. PLoS One. Dec. 20, 2006 ;1:e55.
UK Combined Search Report and Office action dated Jun. 29, 2012 for UK application No. GB1209668.1.
Wang, et al. Quantitative measurement of pathogen-specific human memory T cell repertoire diversity using a CDR3 beta-specific microarray. BMC Genomics. Sep. 19, 2007;8:329.
Dou, et al. Analysis of T cell receptor Vbeta gene usage during the course of disease in patients with chronic hepatitis B. J Biomed Sci. Nov.-Dec. 1998;5(6):428-34.
Pira, et al. Human naive CD4 T-cell clones specific for HIV envelope persist for years in vivo in the absence of antigenic challenge. J Acquir Immune Defic Syndr. Oct. 1, 2005;40(2):132-9.
Ria, et al. Collagen-specific T-cell repertoire in blood and synovial fluid varies with disease activity in early rheumatoid arthritis. Arthritis Res Ther. 2008;10(6):R135. Epub Nov. 17, 2008.
Rickinson, et al. Human cytotoxic T lymphocyte responses to Epstein-Barr virus infection. Annu Rev Immunol. 1997;15:405-31.

(56) References Cited

OTHER PUBLICATIONS

Schaufelberger, et al. An uneven expression of T cell receptor V genes in the arterial wall and peripheral blood in giant cell arteritis. Inflammation. Dec. 2008;31(6):372-83.
Scholler, et al. Analysis of T cell receptor alpha beta variability in lymphocytes infiltrating melanoma primary tumours and metastatic lesions. Cancer Immunol Immunother. Oct. 1994;39(4):239-48.
Struyk, et al. T cell receptors in rheumatoid arthritis. Arthritis Rheum. May 1995;38(5):577-89.
U.S. Appl. No. 13/763,978, filed Feb. 11, 2013, Faham et al.
Alatrakchi, et al. T-cell clonal in patients with B-cell lymphoproliferative disorders. J Immunother. Sep. 1998;21(5):363-70.
Bruggemann, et al. Standardized MRD quantification in European ALL trials: proceedings of the Second International Symposium on MRD assessment in Kiel, Germany, Sep. 18-20, 2008. Leukemia. Mar. 2010;24(3):521-35. doi: 10.1038/leu.2009.268. Epub Dec. 24, 2009.
Gerlinger, et al. How Darwinian models inform therapeutic failure initiated by clonal heterogeneity in cancer medicine. Br J Cancer. Oct. 12, 2010;103(8):1139-43. doi: 10.1038/sj.bjc.6605912. Epub Sep. 28, 2010.
Guo, et al. Sequence changes at the V-D junction of the VH1 heavy chain of anti-phosphocholine antibodies alter binding to and protection against *Streptococcus pneumoniae*. Int Immunol May 1997;9(5):665-77.
Howe, et al. T cell receptor clonotype analysis of T cell responses: Diagnostic application of a clonotypic database. Blood. 2003; 102:Abstract 3918.
Office action dated Mar. 13, 2013 for U.S. Appl. No. 13/763,978.
Office action dated Mar. 20, 2013 for U.S. Appl. No. 13/487,980.
Office action dated Dec. 6, 2012 for U.S. Appl. No. 13/100,395.
Sfanos, et al. Phenotypic analysis of prostate-infiltrating lymphocytes reveals TH17 and Treg skewing. Clin Cancer Res. Jun. 1, 2008;14(11):3254-61. doi: 10.1158/1078-0432.CCR-07-5164.
Sing, et al. A molecular comparison of T lymphocyte populations infiltrating the liver and circulating in the blood of patients with chronic hepatitis B: evidence for antigen-driven selection of a public complementarity-determining region 3 (CDR3) motif. Hepatology. May 2001;33(5):1288-98.
Szczepanski, et al. Comparative analysis of Ig and TCR gene rearrangements at diagnosis and at relapse of childhood precursor-B-ALL provides improved strategies for selection of stable PCR targets for monitoring of minimal residual disease. Blood. Apr. 1, 2002;99(7):2315-23.
Szczepanski, et al. Why and how to quantify minimal residual disease in acute lymphoblastic leukemia? Leukemia. Apr. 2007;21(4):622-6. Epub Feb. 15, 2007.
UK combined search and examination report dated Mar. 20, 2013 for GB 1300533.5.
Van Der Velden, et al. Analysis of minimal residual disease by Ig/TCR gene rearrangements: guidelines for interpretation of real-time quantitative PCR data Leukemia. Apr. 2007;21(4):604-11. Epub Feb. 8, 2007.
Van Der Velden, et al. Detection of minimal residual disease in hematologic malignancies by real-time quantitative PCR: principles, approaches, and laboratory aspects. Leukemia. Jun. 2003;17(6):1013-34.
U.S. Appl. No. 12/945,678, filed Nov. 12, 2010, Faham et al.
U.S. Appl. No. 13/627,497, filed Sep. 26, 2012, Faham et al.
Bagnara, et al. IgV gene intraclonal diversification and clonal evolution in B-cell chronic lymphocytic leukaemia. Br J Haematol. Apr. 2006;133(1):50-8.
Beishuizen, et al. Analysis of Ig and T-cell receptor genes in 40 childhood acute lymphoblastic leukemias at diagnosis and subsequent relapse: implications for the detection of minimal residual disease by polymerase chain reaction analysis. Blood. Apr. 15, 1994;83(8):2238-47.
Davi, et al. Lymphocytic progenitor cell origin and clonal evolution of human B-lineage acute lymphoblastic leukemia. Blood. Jul. 15, 1996;88(2):609-21.
Germano, et al. Clonality profile in relapsed precursor-B-ALL children by GeneScan and sequencing analyses. Consequences on minimal residual disease monitoring. Leukemia. Aug. 2003;17(8):1573-82.
Golembowski, et al. Clonal evolution in a primary cutaneous follicle center B cell lymphoma revealed by single cell analysis in sequential biopsies. Immunobiology. Apr. 2000;201(5):631-44.
Green, et al. Clonal diversity of Ig and T-cell-receptor gene rearrangements identifies a subset of childhood B-precursor acute lymphoblastic leukemia with increased risk of relapse. Blood. Aug. 1, 1998;92(3):952-8.
Gurrieri, et al. Chronic lymphocytic leukemia B cells can undergo somatic hypermutation and intraclonal immunoglobulin V(H)DJ(H) gene diversification. J Exp Med. Sep. 2, 2002;196(5):629-39.
Langerak, et al. Immunoglobulin/T-cell receptor clonality diagnostics. Exoert Opin. Med. Diagn. 2007; 1(3):451-461.
Li, et al. Clonal rearrangements in childhood and adult precursor B acute lymphoblastic leukemia: a comparative polymerase chain reaction study using multiple sets of primers. Eur J Haematol. Oct. 1994;63(4):211-8.
Li, et al. Detailed clonality analysis of relapsing precursor B acute lymphoblastic leukemia: implications for minimal residual disease detection. Leukemia Research. 2001; 25:1033-1045.
Matolcsy, et al. Clonal evolution of B cells in transformation from low- to high-grade lymphoma. Eur J Immunol. Apr. 1999;29(4):1253-64.
Pels, et al. Clonal evolution as pathogenetic machanism in relapse of primary CNS lymphoma. Neurology. Jul. 13, 2004;63(1):167-9.
Rosenquist, et al. Clonal evolution as judged by immunoglobulin heavy chain gene rearrangements in relapsing precursor-B acute lymphoblastic leukemia. Eur J Haematol. Sep. 1999;63(3):171-9.
Ryan, et al. Clonal evolution of lymphoblastoid cell lines. Lab Invest. Nov. 2006;86(11):1193-200. Epub Oct. 2, 2006
Steenbergen, et al. Distinct ongoing Ig heavy chain rearrangement processes in childhood B-precursor acute lymphoblastic leukemia. Blood. Jul. 15, 1993;82(2):581-9.
Steward, et al. A polymerase chain reaction study of the stability of Ig heavy-chain and T-cell receptor delta gene rearrangements between presentation and relapse of childhood B-lineage acute lymphoblastic leukemia. Blood. Mar. 1, 1994;83(5):1355-62.
Qu, et al. Efficient frequency-based de novo short-read clustering for error trimming in next-generation sequencing. Genome Res. Jul. 2009;19(7):1309-15. doi: 10.1101/gr.089151.108. Epub May 13, 2009.

\* cited by examiner

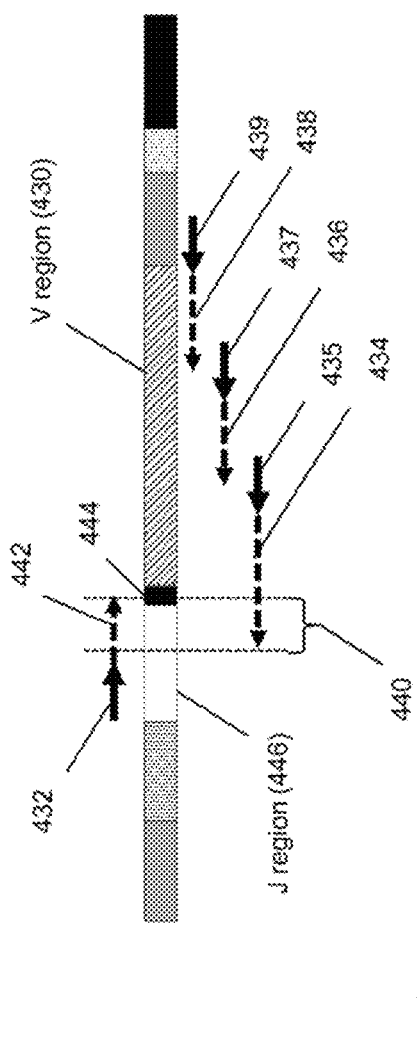
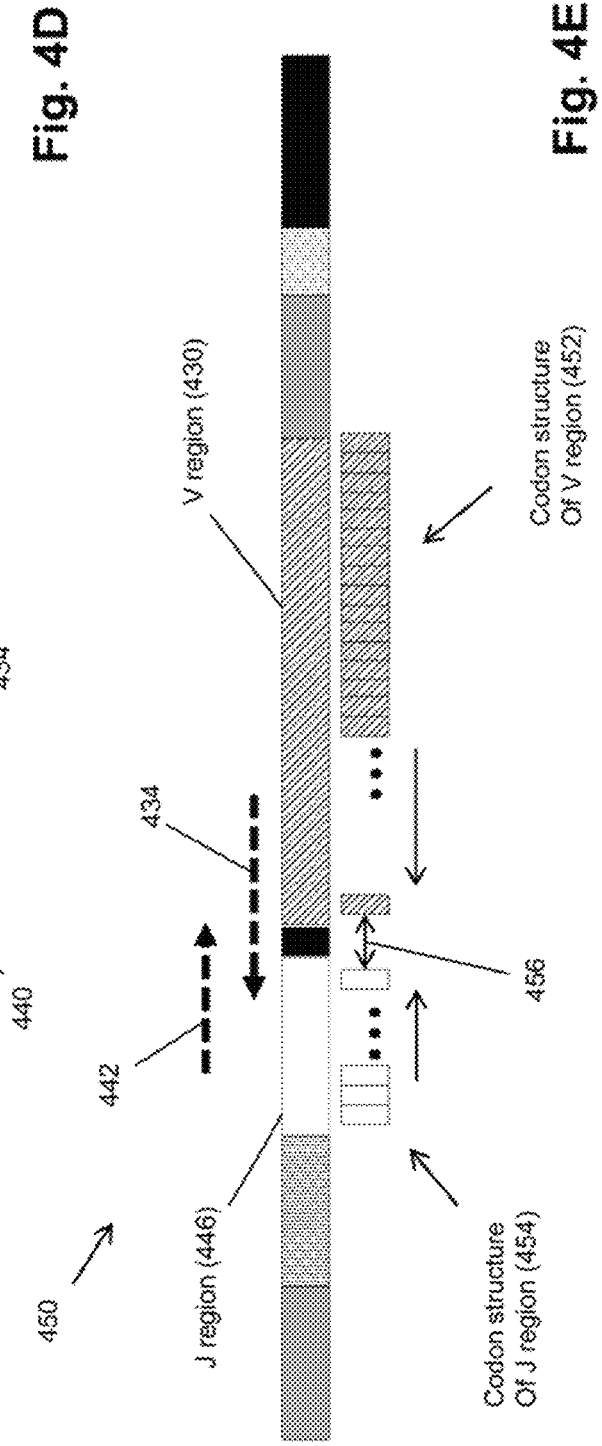

METHOD OF DETERMINING CLONOTYPES AND CLONOTYPE PROFILES

This application is a continuation-in-part of U.S. application Ser. No. 13/100,389 filed 4 May 2011, now U.S. Pat. No. 8,691,510, which is a continuation-in-part of U.S. application Ser. No. 12/615,263 filed 9 Nov. 2009, now U.S. Pat. No. 8,236,503, this application claims benefit of U.S. provisional applications Ser. No. 61/446,822 filed 25 Feb. 2011 and Ser. No. 61/455,743 filed 25 Oct. 2010, the foregoing applications being incorporated by reference in their entireties.

BACKGROUND OF THE INVENTION

Analysis of biological or medical samples often requires the determination of nucleic acid sequences of large and complex populations of DNA and/or RNA, e.g. Gloor et al, PLoS ONE 5(10): e15406 (2010); Petrosino et al, Clinical Chemistry, 55(5): 856-866 (2009); Arstila et al, Science, 286: 958-961 (1999). In particular, profiles of nucleic acids encoding immune molecules, such as T cell or B cell receptors, or their components, contain a wealth of information on the state of health or disease of an organism, so that the use of such profiles as diagnostic or prognostic indicators has been proposed for a wide variety of conditions, e.g. Faham and Willis, U.S. patent publication 2010/0151471; Freeman et al, Genome Research, 19: 1817-1824 (2009); Boyd et al, Sci. Transl. Med., 1(12): 12ra23 (2009); He et al, Oncotarget (Mar. 8, 2011). Such sequence-based profiles are capable of much greater sensitivity than approaches based on size distributions of amplified target nucleic acids, sequence sampling by microarrays, hybridization kinetics curves from PCR amplicons, or other approaches, e.g. Morley et al, U.S. Pat. No. 5,418,134; van Dongen et al, Leukemia, 17: 2257-2317 (2003); Ogle et al, Nucleic Acids Research, 31: e139 (2003); Wang et al, BMC Genomics, 8: 329 (2007); Baum et al, Nature Methods, 3(11): 895-901 (2006). However, the efficient determination of clonotypes and clonotype profiles from sequence data poses challenges because of the size populations to be analyzed, the limited predictability of natural variability in the sequences extracted from samples, and noise introduced into the data by a host of sample preparation and measurement steps, e.g. Warren et al, Genome Research, 21(5): 790-797 (2011).

In view of the potential importance of clonotype profiles for diagnostic and prognostic applications, it would be advantageous to many fields in medicine and biology, if methods were available for overcoming drawbacks of current methodologies for determining clonotypes and clonotype profiles from sequence data.

SUMMARY OF THE INVENTION

The present invention is drawn to methods for producing sequence-based profiles of complex nucleic acid populations. The invention is exemplified in a number of implementations and applications, some of which are summarized below and throughout the specification.

In one aspect, the invention is directed to a method of forming a clonotype profile comprising the steps of (a) forming a data structure of somatically recombined immune molecules from sequence reads thereof, (b) coalescing with a highest frequency candidate clonotype any lesser frequency candidate clonotypes whenever such lesser frequency is below a predetermined frequency value and a sequence difference therebetween is below a predetermined difference value to form a clonotype, (c) removing the coalesced candidate clonotype from the data structure, and (d) repeating steps (b) and (c) until a clonotype profile is formed. In one aspect, such data structure is a sequence tree.

In another aspect, the invention is directed to a method of generating a clonotype profile from an individual comprising the steps of: (a) spatially isolating individual molecules derived from a nucleic acid sample from T-cells and/or B-cells of the individual; (b) sequencing said spatially isolated individual molecules to produce a plurality of sequence reads each having portions of a V region, an NDN region and a J region wherein for each such molecule at least one sequence read encompasses a portion of the NDN region; (c) forming from sequence reads encompassing at least a portion of an NDN region a data structure having elements representing candidate clonotypes, each element and its corresponding candidate clonotype having a frequency; (d) coalescing with a highest frequency candidate clonotype any lesser frequency candidate clonotypes whenever such lesser frequency is below a predetermined frequency value and a sequence difference therebetween is below a predetermined difference value to form a clonotype having a sequence of the highest frequency candidate clonotype; (e) removing elements corresponding to the coalesced candidate clonotypes from the data structure; and (f) repeating steps (d) and (e) until clonotypes have been formed from all non-singleton lesser frequency candidate clonotypes, thereby generating the clonotype profile. In one aspect, the data structure is a sequence tree and the elements corresponding to candidate clonotypes are leaves of the sequence tree.

In another aspect, the invention provides a method for determining clonotypes of an immune repertoire comprising the steps: (a) providing a set of sequence reads from a repertoire of recombined immune molecules each having a V region, an NDN region and a J region wherein for each such molecule at least one sequence read encompasses at least a portion of the NDN region of such molecule; (b) forming from sequence reads encompassing at least a portion of an NDN region a data structure having elements representing candidate clonotypes, each leaf and its corresponding candidate clonotype having a frequency; (c) coalescing with a highest frequency candidate clonotype any lesser frequency candidate clonotypes whenever such lesser frequency is below a predetermined frequency value and a sequence difference therebetween is below a predetermined difference value to form a clonotype having a sequence of the highest frequency candidate clonotype; (d) removing elements corresponding to the coalesced candidate clonotypes from the data structure; and (e) repeating steps (c) and (d) until a highest frequency of a lesser frequency candidate clonotype is below a predetermined stopping value. In one aspect, the data structure is a sequence tree and the elements corresponding to candidate clonotypes are leaves of the sequence tree.

In still another aspect, the invention is directed to a method of determining clonotypes of an immune repertoire comprising the steps: (a) providing a set of sequence reads from a repertoire of recombined immune molecules each having portions of a V region, an NDN region and a J region wherein for each such molecule at least one sequence read encompasses a portion of the NDN region of such molecule; (b) forming from sequence reads encompassing portions of NDN regions a sequence tree having leaves representing candidate clonotypes, each leaf and its corresponding candidate clonotype having a frequency; (c) selecting a highest frequency candidate clonotype and identifying all said lesser frequency candidate clonotypes having a sequence difference therewith less than a predetermined difference value to form a coalescence subset; (d) coalescing with the highest frequency candidate clonotype any lesser frequency candidate clonotypes in the coalescence subset whenever such lesser frequency is below a predetermined frequency value to form a clonotype having a sequence of the highest frequency candidate clonotype (e) removing leaves corresponding to the coalesced candidate clonotypes from the sequence tree; and (f) repeating steps (c) and (e) until clonotypes have been formed from all non-singleton lesser frequency candidate clonotypes.

The present invention provides methods for determining clonotypes and clonotype profiles from large sets of sequence data obtained by high throughput sequencing of somatically recombined immune molecules. In one aspect, the invention implements the above methods by using one or more sequence trees for efficiently carrying out sequence comparisons necessary for distinguishing candidate clonotypes with genuine sequence differences from those with experimental or measurement errors, such as sequencing errors.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

BRIEF DESCRIPTION OF THE DRAWINGS

The novel features of the invention are set forth with particularity in the appended claims. A better understanding of the features and advantages of the present invention is obtained by reference to the following detailed description that sets forth illustrative embodiments, in which the principles of the invention are utilized, and the accompanying drawings of which:

FIG. 4D illustrates the locations of sequence reads generated for an IgH chain. FIG. 4E illustrates the use of the codon structure of V and J regions to improve base calls in the NDN region.

DETAILED DESCRIPTION OF THE INVENTION

The practice of the present invention may employ, unless otherwise indicated, conventional techniques and descriptions of molecular biology (including recombinant techniques), bioinformatics, cell biology, and biochemistry, which are within the skill of the art. Such conventional techniques include, but are not limited to, sampling and analysis of blood cells, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV); *PCR Primer: A Laboratory Manual;* and *Molecular Cloning: A Laboratory Manual* (all from Cold Spring Harbor Laboratory Press); Gusfield, *Algorithms on Strings, Trees, and Sequences* (Cambridge University Press, 1997); and the like.

In one aspect, the invention is directed to a method for obtaining and analyzing sequence data from a repertoire of immune molecules, such as T cell receptors (TCRs), to rapidly and efficiently determine a clonotype profile. Sequence data typically comprises a large collection of sequence reads, i.e. sequences of base calls and associated quality scores. A key challenge in constructing clonotype profiles is to rapidly and accurately distinguish sequence reads that contain genuine differences from those that contain errors from non-biological sources, such as the sequencing chemistry, amplification chemistry, or the like. An aspect of the invention is the use of sequence trees to represent and organize sequence data from immune molecules extracted from a sample. Such immune molecules typically form an immune repertoire which comprises a very large set of very similar polynucleotides (e.g. >1000, but more usually from 100,000 to 1,000,000, or more) which are relatively short in length (e.g. usually less than 300 bp). In one aspect of the invention, the inventors recognized and appreciated that these characteristics permitted the use of sequence tree data structures to efficiently compare sequence reads and candidate clonotypes as compared with analytical approaches using other data structures, e.g. lists, arrays, hash table, or the like.

Figure 1A:
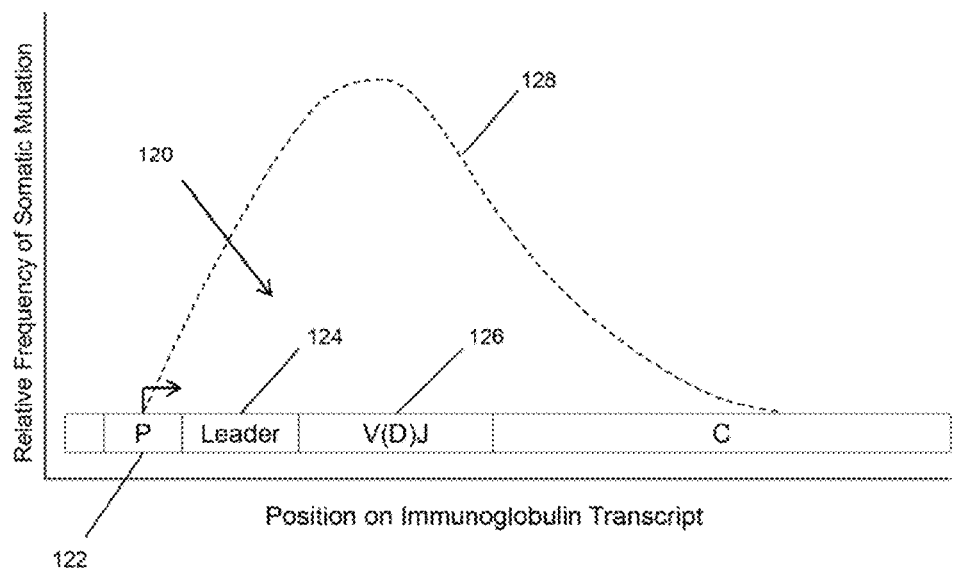
FIG. 1A illustrates an IgH transcript and sources of natural variability within it.

The enormous complexity of immune repertoires is well-known, e.g. Arstila et al, Science, 286: 958-961 (1999) and Warren et al (cited above). FIG. 1A illustrates diagrammatically a typical transcript of an IgH molecule (120) from which a clonotype profile is derived in accordance with some embodiments of the invention. Sources of natural sequence variability include modular recombination of the C, D, J and V segments from large sets carried by the genome, nucleotide additions and deletions to the ends of the D segment to produce the so-called "NDN" regions, and somatic hypermutation where substitutions are made randomly over the length of transcript (122) at a relative frequency roughly as indicated by curve (128). In one aspect of the invention, complex populations of such IgH and TCR transcripts are amplified and sequenced. In one aspect one or both operations for IgH molecules are carried out by using redundant primers annealing to different sites in the V regions (described more fully below). This is particularly advantageous where a sequencing chemistry is employed that has a relatively high error rate or where such sequence variability is difficult or impossible to know beforehand. In the latter case, primer extension for amplification or generation of sequence reads takes place even if one or more primer binding sites are inoperable, or substantially inoperable, because of mismatches caused (for example) by one or more somatic mutations. Starting from promoter P (122) relative frequency shown by curve (128) climbs through leader region (124) to a maximum over the V(D)J region (126) of the transcript after which it drop to near zero. In one aspect of the invention, a segment of recombined B cell nucleic acid is amplified by a PCR with a plurality of forward primers or a plurality of reverse primers to generate a nested set of templates (see FIGS. 4A and 4B and their descriptions below). Templates from such a set may be further amplified on a surface to form separate amplicons (e.g. by bridge PCR using a cBot instrument, Illumina, San Diego, Calif.). Templates from the same nested set may be associated with one another by sequence reads generated at their common ends. Nested sets of templates allow a sequencing chemistry with relative high error rates to be used to analyze longer sequences than otherwise would be possible, while at the same time maintaining high average quality scores over the entire length of the sequence. The nested sets also ensure that at least one sequence read is obtained from a V region even if it has been subjected to somatic hypermutation. In one embodiment, sequencing chemistries may be used for analyzing highly variable nucleic acids, such as IgH molecules, that have error rates no better than the following: 0.2 percent of sequence reads contain at least one error in positions 1-50; 0.2-1.0 percent of sequence reads contain at least one error in positions 51-75; 0.5-1.5 percent of sequence reads contain at least one error in positions 76-100; and 1-5 percent of sequence reads contain at least one error in positions 101-125. In view of the above, the method of the invention includes steps for distinguishing clonotype sequences that are closely related and genuinely different from those that are closely related and the result of sequencing or other error.

Constructing clonotypes from sequence read data depends in part on the sequencing method used to generate such data, as the different methods have different expected read lengths and data quality. In one approach, a Solexa sequencer is employed to generate sequence read data for analysis. In one embodiment, a sample is obtained that provides at least 0.5-1.0×10$^6$ lymphocytes to produce at least 1 million template molecules, which after optional amplification may produce a corresponding one million or more clonal populations of template molecules (or clusters). For most high throughput sequencing approaches, including the Solexa approach, such over sampling at the cluster level is desirable so that each template sequence is determined with a large degree of redundancy to increase the accuracy of sequence determination. For Solexa-based implementations, preferably the sequence of each independent template is determined 10 times or more. For other sequencing approaches with different expected read lengths and data quality, different levels of redundancy may be used for comparable accuracy of sequence determination. Those of ordinary skill in the art recognize that the above parameters, e.g. sample size, redundancy, and the like, are design choices related to particular applications.

Figure 1B:
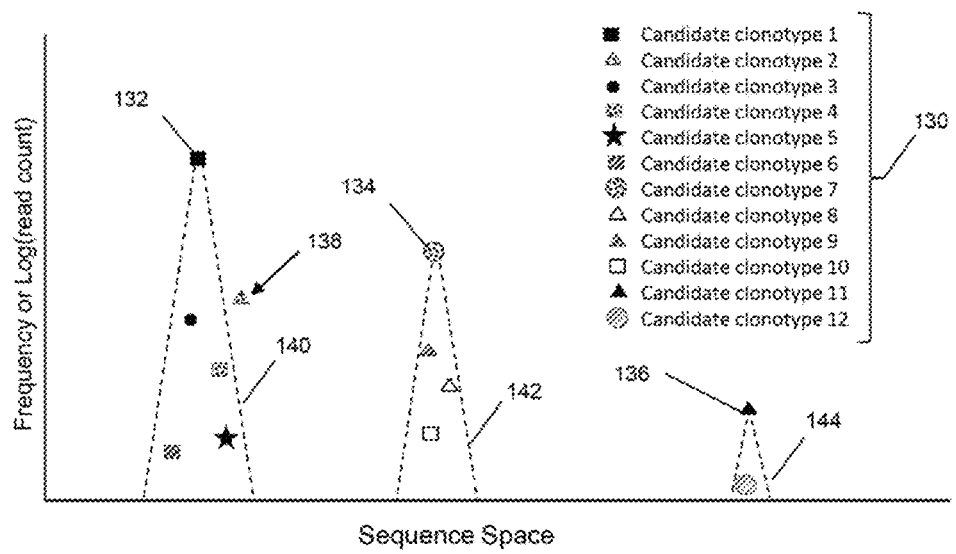
FIG. 1B illustrates concepts of clonotypes in sequence space and distances between closely related clonotypes.

Reducing a set of reads for a given sample to a set of distinct clonotypes and recording the number of reads for each clonotype would be a trivial computational problem if sequencing technology was error free. However, in the presence of sequencing errors, each genuine clonotype is surrounded by a 'cloud' of reads with, varying numbers of errors with respect to the its sequence. The "cloud" of sequencing errors drops off in density as the distance increases from the clonotype in sequence space. A variety of algorithms are available for converting sequence reads into clonotypes. In one aspect, coalescing of sequence reads (that is, merging candidate clonotypes determined to have one or more sequencing errors) depends on at least three factors: the number of sequences obtained for each of the clonotypes being compared; the number of bases at which they differ; and the sequencing quality score at the positions at which they are discordant. A likelihood ratio may be constructed and assessed that is based on the expected error rates and binomial distribution of errors. For example, two clonotypes, one with 150 reads and the other with 2 reads with one difference between them in an area of poor sequencing quality will likely be coalesced as they are likely to be generated by sequencing error. On the other hand two clonotypes, one with 100 reads and the other with 50 reads with two differences between them are not coalesced as they are considered to be unlikely to be generated by sequencing error. In one embodiment of the invention, the algorithm described below may be used for determining clonotypes from sequence reads. Some of these concepts are illustrated in FIG. 1B. In one aspect of the invention, sequence reads are first converted into candidate clonotypes. Such a conversion depends on the sequencing platform employed. For platforms that generate high Q score long sequence reads, the sequence read or a portion thereof may be taken directly as a candidate clonotype. For platforms that generate lower Q score shorter sequence reads, some alignment and assembly steps may be required for converting a set of related sequence reads into a candidate clonotype. For example, for Solexa-based platforms, in some embodiments, candidate clonotypes are generated from collections of paired reads from multiple clusters, e.g. 10 or more, as mentioned above. The frequencies of candidate clonotypes may be plotted in sequence space, as illustrated in FIG. 1B, where such space is reduced to one dimension (the horizontal axis) for sake of illustration. The vertical axis gives the magnitude of each candidate clonotype's frequency, log(read count), or some like measure. In the figure, candidate clonotypes are represented by the various symbols (130). In accordance with one embodiment of the invention, whether two candidate clonotypes are coalesced depends on their respective frequencies or read counts (as noted above), the number of base differences between them (the more differences, the less likely is coalescence), and the quality scores of the bases at the locations where the respective sequences differ (higher quality scores makes coalescence less likely). Candidate clonotypes may be considered in the order of their respective frequencies. FIG. 1B shows candidate clonotype 1 (132), candidate clonotype 7 (134) and candidate clonotype 1 (136) as the three candidates with the highest three frequencies. Related to each such candidate clonotype are other candidate clonotypes that are close in sequence, but with lesser frequencies, such as (i) for candidate clonotype 1 (132) there are candidate clonotype 2 (138) and the candidate clonotypes 3, 4, 5 and 6 enclosed by cone (140); for candidate clonotype 7 (134) there are candidate clonotypes 8, 9 and 10 enclosed by cone (142); and (iii) for candidate clonotype 11, there is candidate clonotype 12 enclosed by cone (144). The cones represent likelihood boundaries within which a lesser frequency candidate clonotype would be coalesced with one of the higher frequency candidate clonotypes 1, 7 or 11. Such likelihood boundaries are functions of the frequency of the nearby candidate clonotypes (3, 4, 5 and 6 for 1; 8, 9 and 10 for 7; and 12 for 11) and their distances in sequence space from the respective higher frequency candidate clonotypes. Candidate clonotype 2 (138) is outside cone (140); thus, it would not be coalesced with candidate clonotype 1 (132). Again, the likelihood (of coalesce) boundaries are shown as cones because candidate clones with higher frequencies are more likely to be genuinely different clonotypes than those of lower frequencies and multiple differences at lower frequencies are more likely to be errors than multiple differences at higher frequencies.

The cloud of sequence reads surrounding each candidate clonotype can be modeled using the binomial distribution and a simple model for the probability of a single base error. This latter error model can be inferred from mapping V and J segments or from the clonotype finding algorithm itself, via self-consistency and convergence. A model is constructed for the probability of a given 'cloud' sequence Y with read count C2 and E errors (with respect to sequence X) being part of a true clonotype sequence X with perfect read count C1 under the null model that X is the only true clonotype in this region of sequence space. A decision is made whether or not to coalesce sequence Y into the clonotype X according the parameters C1, C2, and E. For any given C1 and E a max value C2 is pre-calculated for deciding to coalesce the sequence Y. The max values for C2 are chosen so that the probability of failing to coalesce Y under the null hypothesis that Y is pan of clonotype X is less than some value P after integrating overall possible sequences Y with error E in the neighborhood of sequence X. The value P is controls the behavior of the algorithm and makes the coalescing more or less permissive.

If a sequence Y is not coalesced into clonotype X because its read count is above the threshold C2 for coalescing into clonotype X then it becomes a candidate for seeding separate clonotypes (such as with candidate clonotype 2 (138) in FIG. 1B). An algorithm implementing such principles would also make sure that any other sequences Y2, Y3, etc. which are 'nearer' to this sequence Y (that had been deemed independent of X) are not aggregated into X. This concept of 'nearness' includes both error counts with respect to Y and X and the absolute read count of X and Y, i.e. it is modeled in the same fashion as the above model for the cloud of error sequences around clonotype X. In this way 'cloud' sequences can be properly attributed to their correct clonotype if they happen to be 'near' more than one clonotype. Thus, going to FIG. 1B, if candidate clonotype 2 is deemed to be genuinely distinct from candidate clonotype 1 (132), then a special routine, or subalgorithm, would provide a rule for determining which of candidate clonotypes 1 (132) and 2 (138), candidates 4 and 3, between 1 and 2, should be coalesced to (if either).

In one embodiment, an algorithm proceeds in a top down fashion by starting with the sequence X with the highest read count. This sequence seeds the first clonotype. Neighboring sequences are either coalesced into this clonotype if their counts are below the precalculated thresholds (see above), or left alone if they are above the threshold or 'closer' to another sequence that was not coalesced. After searching all neighboring sequences within a maximum error count, the process of coalescing reads into clonotype X is finished. Its reads and all reads that have been coalesced into it are accounted for and removed from the list of reads available for making other clonotypes. The next sequence is then moved on to with the highest read count. Neighboring reads are coalesced into this clonotype as above and this process is continued until there are no more sequences with read counts above a given threshold, e.g. until all sequences with more than 1 count have been used as seeds for clonotypes.

As mentioned above, in anther embodiment of the above algorithm, a further test may be added for determining whether to coalesce a candidate sequence Y into an existing clonotype X, which takes into account quality score of the relevant sequence reads. The average quality score(s) are determined for sequence(s) Y (averaged across all reads with sequence Y) were sequences Y and X differ. If the average score is above a predetermined value then it is more likely that the difference indicates a truly different clonotype that should not be coalesced and if the average score is below such predetermined value then it is more likely that sequence Y is caused by sequencing errors and therefore should be coalesced into X.

Successful implementation of the above algorithm for coalescing candidate clonotypes is dependent upon having an efficient way of finding all sequences with less than E errors (i.e. less than some sequence distance measure) from some input sequence X. This problem is solved using a sequence tree. The implementation of such trees has some unusual features in that the nodes of the tree are not restricted to being single letters of the DNA sequences of the candidate clonotypes, as illustrated in FIG. 1E. The nodes can have arbitrarily long sequences, which allows for a more efficient use of computer memory.

All of the reads of a given sample are placed into the sequence tree. Each leaf nodes holds pointers to its associated reads. A unique sequence of a candidate clonotype is retrieved by traversing backwards in the tree from the leaf to the root node. The first sequence is placed into a simple tree with one root node and one leaf node that contains the full sequence of the read. Sequences are next added one by one. For each added sequence either a new branch is formed at the last point of common sequence between the read and the existing tree or add the read to an existing leaf node if the tree already contains the sequence. Having placed all the reads into the tree it is easy to use the tree for the following purposes 1) Finding the highest read count: sorting leaf nodes by read count allows one to find the leaf node (i.e. sequence) with the most reads, and successively lower numbers of reads; 2) Finding neighboring leafs: for any sequence all paths through the tree which have less than X errors with respect to this sequence are searchable. A path is started at the root and branch this path into separate paths proceeding along the tree. The current error count of each path as proceeding along the tree is noted. When the error count exceeds the max allowed errors the given path is terminated. In this way large parts of the tree are pruned as early as possible. This is an efficient way of finding all paths (i.e. all leafs) within X errors from any given sequence.

Figure 1C:
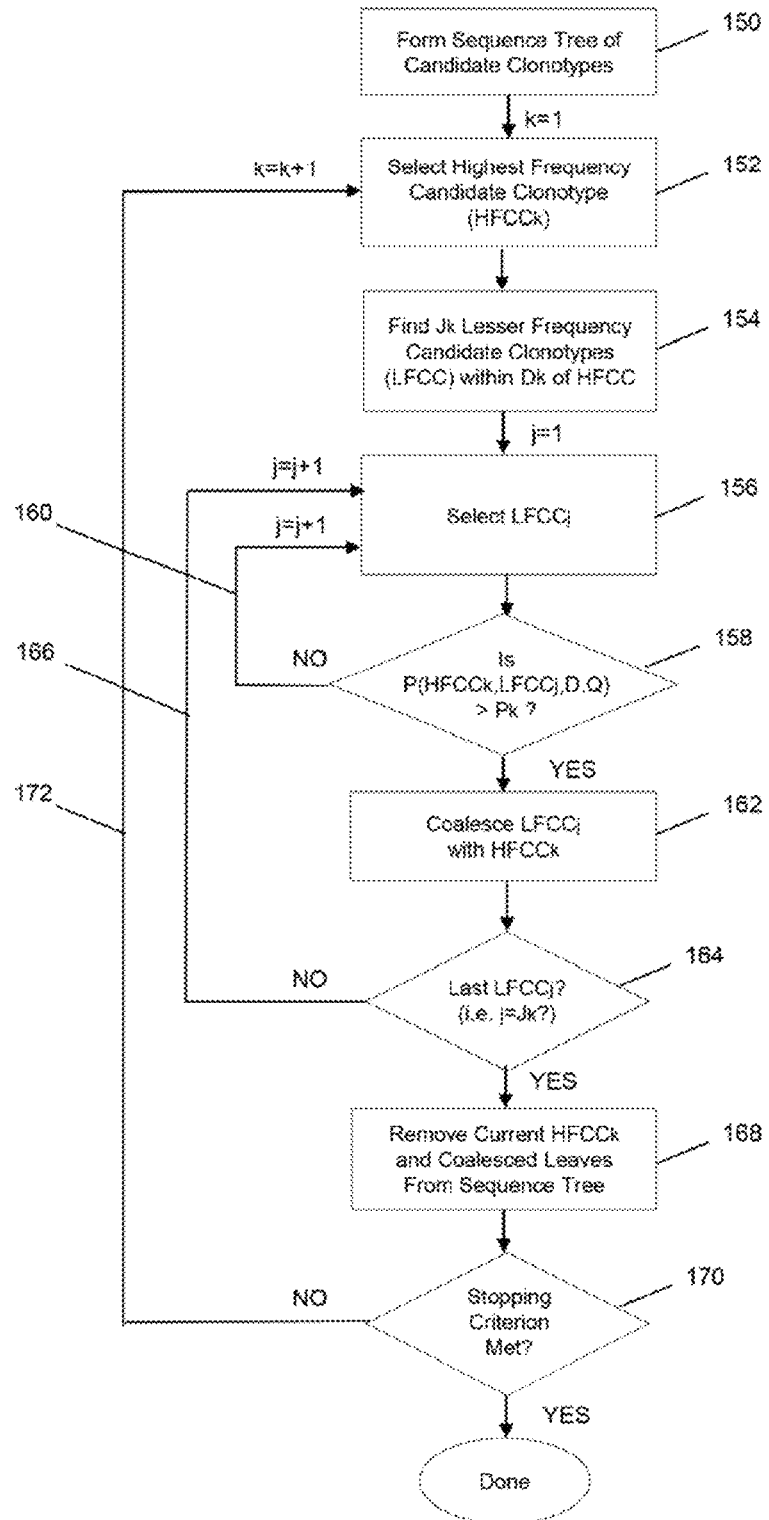
FIG. 1C is a flow chart illustrating one embodiment of a method for distinguishing genuinely different clonotypes from clonotypes that differ solely by sequencing errors (Which should be coalesced).
Figure 1D:
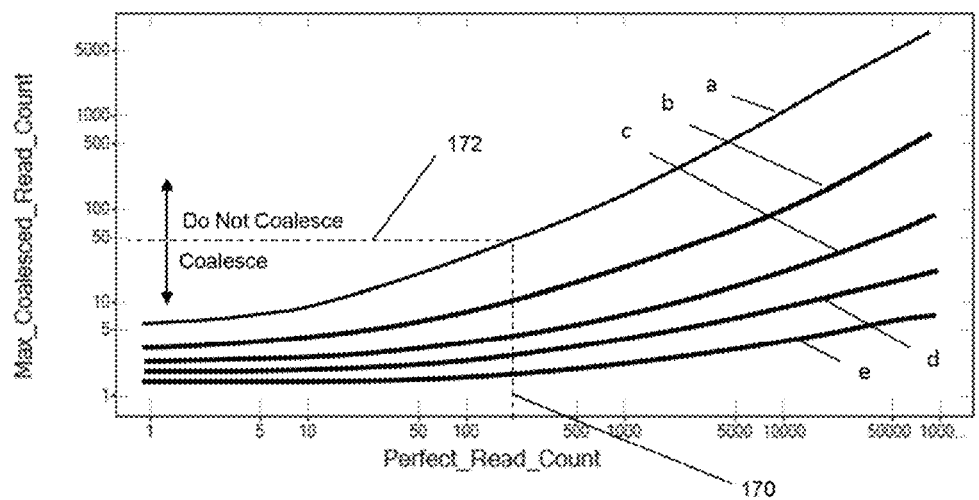
FIG. 1D illustrates the form of a numerical function used in one embodiment for determining whether or not to coalesce related clonotypes.
Figure 1E:
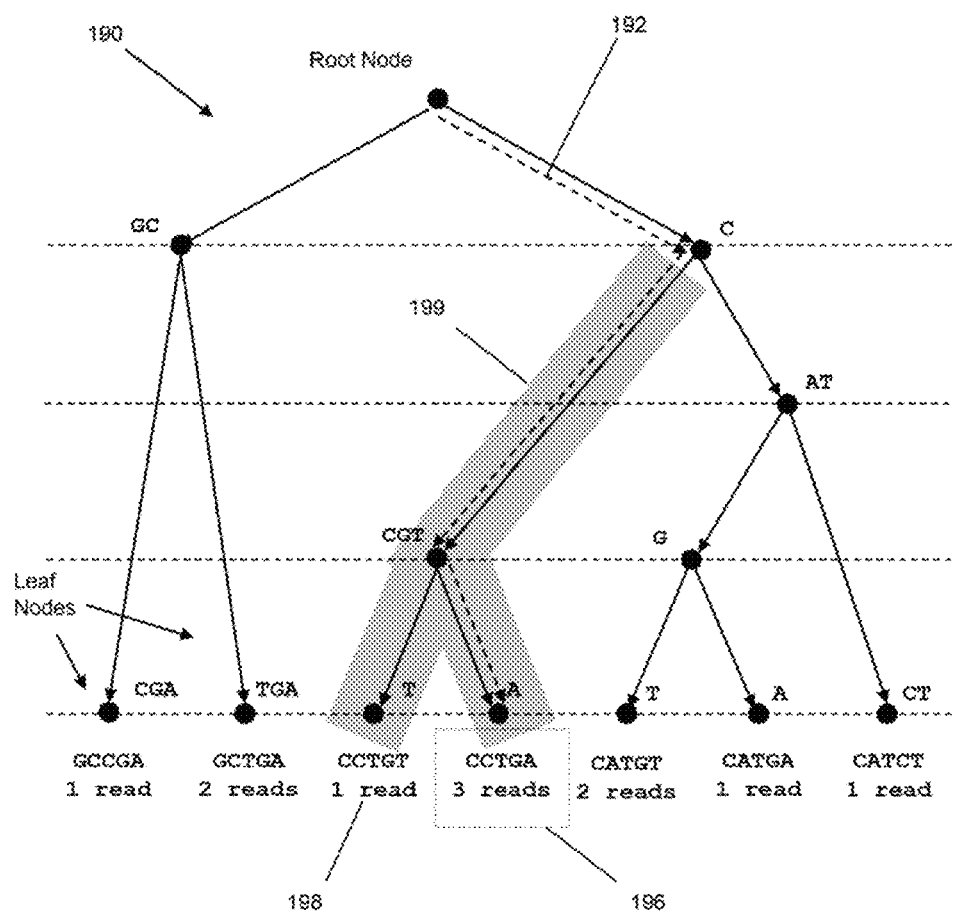
FIGS. 1E-1F illustrate the use of sequence trees in the methods of the invention.

Features of the above concepts are illustrated in more detail in the flow chart of FIG. 1C. A set of candidate clonotypes is obtained from sequence data obtained by sequencing recombined nucleic acids extracted from a sample of T cells or B cells. In one aspect, candidate clonotypes each include an NDN region and portions of V and J regions. These sequences are organized into a data structure (150), which may be a sequence tree. Not shown in FIG. 1C, as part of generating a set of candidate clonotypes, in one embodiment, sequence trees may also be constructed for known V regions and known J regions. Sequence reads making up a candidate clonotype may then be mapped, or aligned, to these known sequences via the sequence trees to efficiently determine the most likely known V and J sequences of the candidate clonotypes. Returning to FIG. 1C, once the candidate clonotype are generated, a data structure, such as a sequence tree, is constructed for use in a method for distinguishing genuine clonotypes from candidate clonotypes that contain experimental or measurement errors, such as sequencing errors. The candidate clonotype that has the highest frequency of occurrence among the current candidate clonotypes ($HFCC_k$) is selected (152) from the data structure, for example a sequence tree; in other words, $HFCC_k$ is the candidate clonotype with the highest number of copies, or read counts in cycle k. Next, neighboring lesser frequency candidate clonotypes are identified (LFCCs) (154); that is, candidate clonotypes within a distance of $D_k$ are identified. In one aspect of the invention, this identification is carried out using a sequence tree, which allows efficient sequence comparisons of relatively short (<300 bp) sequences. In one embodiment, the comparisons, or sequence alignments, are carried out using dynamic programming, e.g. as disclosed by Gusfield (cited above). In a further embodiment, such dynamic programming is banded dynamic programming where sequences that differ from the selected HFCC by more than a predetermined distance are not considered, which speeds the computation. The candidates $HFCC_k$ and $LFCC_j$ may be compared on the basis of many different criteria or properties. In one aspect, as mentioned above, candidate clonotypes are compared on the basis of at least two properties: (i) frequency or read counts and (ii) sequence differences. In another aspect, as mentioned above, candidate clonotypes are compared on the basis of at least three properties: (i) frequency or read counts, (ii) sequence differences, and (iii) quality scores or measures of the bases where differences occur. In one embodiment, sequence differences include base substitutions; in another embodiment, sequence differences include base substitutions, deletions and insertions. The latter embodiment is especially applicable whenever sequence data is generated by sequencing-by-synthesis chemistries that do not employ terminators, such as 454 sequencers and Ion Torrent sequencers. Such sequencing approaches differentiate different sized homopolymer stretches by signal amplitude; thus, base-calling routines in such approaches are prone to insertion and deletion errors, because the difference in signal level from homopolymers differing by one nucleotide drops precipitously with increasing homopolymer size (that is, a 2-mer is readily distinguished from a 3-mer, but an 8-mer is almost indistinguishable from a 9-mer). In one aspect, comparisons of HFCCs and LFCCs may be implemented using a function, such as $P(HFCC_k, LFCC_j, D Q)$ shown in decision box (158), which depends on the quantities (i) through (iii) described above. Such a function may take many different forms, but generally the value of P changes with changes in (i), (ii) and (iii) as follows: The value of P preferably increases monotonically with the frequency of HFCC and the ratio of the frequency of HFCC to that of LFCC, such that the higher the ratio of the frequency of HFCC to that of LFCC, the higher the likelihood LFCC will be coalesced into HFCC. Likewise, the value of P preferably decreases monotonically with degree to which the sequences of HFCC and LFCC differ, so that the greater the difference between HFCC and LFCC (e.g. as measured by the minimal number of substitutions, insertions or deletions to change one to the other) the lower the likelihood LFCC will be coalesced with HFCC. Finally, the value of P preferably decreases monotonically with increasing quality scores of the locations where the sequences of HFCC and LFCC differ, so that for higher quality scores, the lower the likelihood LFCC will be coalesced with HFCC. When the sequences of HFCC and LFCC differ at more than one location, the quality scores at the different locations may be combined in a variety of differ ways. In one embodiment, whenever there is a plurality of such differences, the plurality of quality scores is expressed as an average value, which may be either an unweighted average or a weighted average. FIG. 1D shows an exemplary function, P, computed for different quality values (curves a through e) for a given sequence difference. As illustrated in FIG. 1D, whenever HFCC is at a level of about 200 read counts (170), then if the quality scores are determined by curve (a), any LFCC with less than about 50 read counts (172) are coalesced into HFCC. The argument, D, of function P is a measure of the distance between the sequences $HFCC_k$ and $LFCC_j$ and its value may vary from cycle to cycle as an analysis progresses. (The indices "k" indicates that the values of constants with a "k" subscript may depend on the computational cycle, k.) In one embodiment, $D=D_k$, so that its value is a function of cycle number. In another embodiment, $D=D$ (HFCC frequency), so that its value is a function of the frequency of HFCC; independent of cycle number. For example, as the frequency of HFCC decreases, then distance, D, of candidates to be compared decreases. In one embodiment, D is a Hamming distance between $HFCC_k$ and $LFCC_j$; however, other distance measures may be used. In one embodiment, $D_k$ is a non-increasing function of k; and in another embodiment, $D_k$ is a decreasing function of k. Decreasing the magnitude of D with increasing cycle number, or with decreasing frequency of HFCC, is advantageous in some embodiments because as a computation progresses to lower and lower frequency candidate clonotypes most such candidates are singletons, so that sequence distance (rather than frequency difference) becomes the predominant comparison. By lowering D as the computation progresses, unproductive comparisons to distant low frequency candidate clonotypes are reduced, thereby speeding up the computation. Function P may be a complicated expression depending on the number of factors being considered. FIG. 1D illustrates computed values for one embodiment of P which relates read count thresholds for coalescing an LFCC given a read count of an HFCC for different quality scores, as described above. Curves "a" through "e" represent the relationships for different quality scores (with curve "a" corresponding to the highest quality score).

Figure 1F:
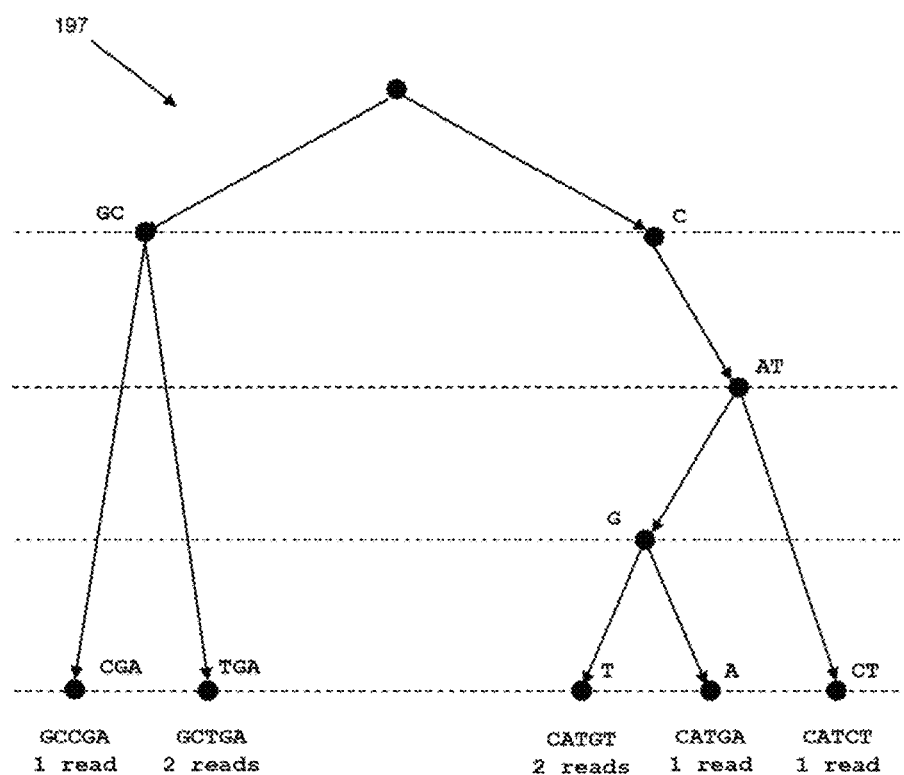

Returning to FIG. 1C, if $P<P_k$, then $LFCC_j$ is not coalesced with $HFCC_k$ and another LFCC is selected (160). If $P>P_k$, then $LFCC_j$ is coalesced with $HFCC_k$ (162), in which case another LFCC is selected (166), unless there are no more LFCC left to evaluate (164). If there are no more LFCC to evaluate (164), then the current $HFCC_k$ (including all of the LFCC's coalesced into it) is removed (168) from the data structure, such as the sequence tree. Such removal is illustrated in the simple sequence tree (190) of FIGS. 1E-F. There, path (192) (indicated by dashed line) in sequence tree (190) corresponds to HFCC (196), which is coalesced with LFCC (198). After coalescence, the segment of path (192) in shaded area (199) is removed from sequence tree (190) to give reduced sequence tree (197) shown in FIG. 1F, which is used in subsequent computations to find neighboring LFCC (154). Ater such removal, clonotype determination is finished if a stopping criterion (170) is met. In one embodiment, stopping criterion (170) is whether the last non-singleton candidate clonotype has been processed (152). In another embodiment, stopping criterion (170) is whether the frequency or the read counts of the selected HFCC is below that corresponding to a single lymphocyte. In one aspect of the method of the invention, an amplification step may result in each lymphocyte in a sample being represented by multiple copies of the same clonotype; thus, in one embodiment, whatever HFCC has a number of read counts below the number corresponding to a single lymphocyte, then the computation is stopped. In some embodiments, such a number of read counts (or candidate clonotype copies) is 10; in another embodiment, such number is 20; in another embodiment, such a number is 30; in another embodiment, such a number is 40. If the stopping criterion is not met, then the next HFCC is selected (172). The analytical steps summarized in the flow chart of FIG. 1C may be implemented in any suitable programming language, such as C, C++, Java, C#. Fortran, Pascal or the like.

In accordance with one aspect of the invention; the above method for determining clonotypes and/or clonotype profiles comprises steps of (a) forming a data structure of recombined immune molecules from sequence reads obtained by high throughput nucleic acid sequencing, (b) coalescing with a highest frequency candidate clonotype any lesser frequency candidate clonotypes whenever such lesser frequency is below a predetermined frequency value and a sequence difference therebetween is below a predetermined difference value to form a clonotype, (c) removing the coalesced candidate clonotype from the data structure, and (d) repeating steps (b) and (c) until a clonotype profile is formed. In one embodiment, the data structure is a sequence tree.

In accordance with another aspect of the invention, the above method of determining clonotypes may be carried out by steps comprising: (a) providing a set of sequence reads from a repertoire of recombined immune molecules each having a V region, an NDN region and a J region wherein for each such molecule at least one sequence read encompasses at least a portion of the NDN region of such molecule; (b) forming from sequence reads encompassing at least a portion of an NDN region a sequence tree having leaves representing candidate clonotypes, each leaf and its corresponding candidate clonotype having a frequency; (c) coalescing with a highest frequency candidate clonotype any lesser frequency candidate clonotypes whenever such lesser frequency is below a predetermined frequency value and a sequence difference therebetween is below a predetermined difference value to form a clonotype having a sequence of the highest frequency candidate clonotype; (d) removing leaves corresponding to the coalesced candidate clonotypes from the sequence tree; and (e) repeating steps (c) and (d) until a highest frequency of a lesser frequency candidate clonotype is below a predetermined stopping value. In one embodiment, the step of forming further includes selecting a highest frequency candidate clonotype and identifying all said lesser frequency candidate clonotypes having a sequence difference therewith less than a predetermined difference value to form a coalescence subset. Thus, in such embodiment, one may limit the total number of LFCCs that must be compared for the coalescing operation (only ones within the predetermined difference value are considered). Such value is a process input depending on the application, e.g. the size of the repertoire, how much computing time is used, and so on. As mentioned above, the function used for deciding whether to coalesce an HFCC with a LFCC can have a variety of forms. In one general aspect, for the step of coalescing, such a function may have the following properties: It depends on frequencies of HFCC, LFCC, the sequence difference therebetween (which may be expressed as a conventional string difference measure, such as a Hamming distance) and quality scores of the one or more nucleotide locations where the HFCC and LFCC differ; such that the function (i) monotonically increases with increasing ratio of frequency of HFCC and frequency of LFCC, (ii) monotonically decreases with increasing sequence difference between HFCC and LFCC, and (iii) monotonically decreases with increasing quality scores of the one or more nucleotide locations. That is, in regard to property (iii), the surer one is that HFCC and LFCC are different (e.g., because there is a high level of confidence in the base calls), then the less likely they will be coalescenced.

In the foregoing, selection of a predetermined frequency value and a predetermined difference value is a design choice that depend on particular applications. Factors affecting such choices may include details of the biology, speed of implementation, and the like.

Samples

Complex populations of nucleic acids for analysis may arise from a variety of sources. Immune system repertoires may be obtained from samples of immune cells. For example, immune cells can include T-cells and/or B-cells. T-cells (T lymphocytes) include, for example, cells that express T cell receptors. T-cells include helper T cells (effector T cells or Th cells), cytotoxic T cells (CTLs), memory T cells, and regulatory T cells. In one aspect a sample of T cells includes at least 1,000 T cells; but more typically, a sample includes at least 10,000 T cells, and more typically, at least 100,000 T cells. In another aspect, a sample includes a number of T cells in the range of from 1000 to 1,000,000 cells. A sample of immune cells may also comprise B cells. B-cells include, for example, plasma B cells, memory B cells, B1 cells, B2 cells, marginal-zone B cells, and follicular B cells. B-cells can express immunoglobulins (antibodies, B cell receptor). As above, in one aspect a sample of B cells includes at least 1,000 B cells; but more typically a sample includes at least 10,000 B cells, and more typically, at least 100,000 B cells. In another aspect, a sample includes a number of B cells in the range of from 1000 to 1,000,000 B cells.

The sample can include nucleic acid, for example, DNA (e.g., genomic DNA or mitochondrial DNA) or RNA (e.g., messenger RNA or microRNA). The nucleic acid can be cell-free DNA or RNA, e.g. extracted from the circulatory system, Vlassov et al, Curr. Mol. Med., 10: 142-165 (2010); Swarup et al, FEBS Lett., 581: 795-799 (2007). In the methods of the provided invention, the amount of RNA or DNA from a subject that can be analyzed includes, for example, as low as a single cell in some applications (e.g., a calibration test) and as many as 10 million of cells or more translating to a range of DNA of 6 pg-60 ug, and RNA of approximately 1 pg-10 ug.

As discussed more fully below (Definitions), a sample of lymphocytes is sufficiently large so that substantially every T cell or B cell with a distinct clonotype is represented therein, thereby forming a repertoire (as the term is used herein). In one embodiment, a sample is taken that contains with a probability of ninety-nine percent every clonotype of a population present at a frequency of 0.001 percent or greater. In another embodiment, a sample is taken that contains with a probability of ninety-nine percent every clonotype of a population present at a frequency of 0.0001 percent or greater. In one embodiment, a sample of B cells or T cells includes at least a half million cells, and in another embodiment such sample includes at least one million cells.

Whenever a source of material from which a sample is taken is scare, such as, clinical study samples, or the like, DNA from the material may be amplified by a non-biasing technique, such as whole genome amplification (WGA), multiple displacement amplification (MDA); or like technique, e.g. Hawkins et al, Curr. Opin. Biotech. 13: 65-67 (2002); Dean et al, Genome Research, 11: 1095-1099 (2001); Wang et al, Nucleic Acids Research, 32: e76 (2004); Hosono et al. Genome Research, 13: 954-964 (2003); and the like.

Blood samples are of particular interest, especially in monitoring lymphoid neoplasms, such as lymphomas, leukemias, or the like, add may be obtained using conventional techniques, e.g. Innis et al, editors, PCR Protocols (Academic Press, 1990); or the like. For example, white blood cells may be separated from blood samples using convention techniques, e.g. RosettSep kit (Stem Cell Technologies, Vancouver, Canada). Blood samples may range in volume from 100 µL to 10 mL; in one aspect, blood sample volumes are in the range of from 200 100 µL to 2 mL. DNA and/or RNA may then be extracted from such blood sample using conventional techniques for use in methods of the invention, e.g. DNeasy Blood & Tissue Kit (Qiagen, Valencia, Calif.). Optionally, subsets of white blood cells, e.g. lymphocytes, may be further isolated using conventional techniques, e.g. fluorescently activated cell sorting (FACS) (Becton Dickinson, San Jose, Calif.), magnetically activated cell sorting (MACS) (Miltenyi Biotec, Auburn, Calif.), or the like.

Since the identifying recombinations are present in the DNA of each individual's adaptive immunity cell as well as their associated RNA transcripts, either RNA or DNA can be sequenced in the methods of the provided invention. A recombined sequence from a T-cell or B-cell encoding a T cell receptor or immunoglobulin molecule, or a portion thereof, is referred to as a clonotype. The DNA or RNA can correspond to sequences from T-cell receptor (TCR) genes or immunoglobulin (Ig) genes that encode antibodies. For example, the DNA and RNA can correspond to sequences encoding $\alpha$, $\beta$, $\gamma$, or $\delta$ chains of a TCR. In a majority of T-cells, the TCR is a heterodimer consisting of an $\alpha$-chain and $\beta$-chain. The TCR$\alpha$ chain is generated by VJ recombination, and the $\beta$ chain receptor is generated by V(D)J recombination. For the TCR$\beta$ chain, in humans there are 48 V segments, 2 D segments, and 13 J segments. Several bases may be deleted and others added (called N and P nucleotides) at each of the two junctions. In a minority of T-cells, the TCRs consist of $\gamma$ and $\delta$ delta chains. The TCR$\gamma$ chain is generated by VJ recombination, and the TCR$\delta$ chain is generated by V(D)J recombination (Kenneth Murphy, Paul Travers, and Mark Walport, *Janeway's Immunology* 7th edition, Garland Science, 2007, which is herein incorporated by reference in its entirety).

The DNA and RNA analyzed in the methods of the invention can correspond to sequences encoding heavy chain immunoglobulins (IgH) with constant regions ($\alpha$, $\delta$, $\epsilon$, $\gamma$, or $\mu$) or light chain immunoglobulins (IgK or IgL) with constant regions $\gamma$ or $\kappa$. Each antibody has two identical light chains and two identical heavy chains. Each chain is composed of a constant (C) and a variable region. For the heavy chain, the variable region is composed of a variable (V), diversity (D), and joining (J) segments. Several distinct sequences coding for each type of these segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site. Added to this diversity is a process of somatic hypermutation which can occur after a specific response is mounted against some epitope.

As mentioned above, in accordance with the invention, primers may be selected to generate amplicons of subsets of recombined nucleic acids extracted from lymphocytes. Such subsets may be referred to herein as "somatically rearranged regions." Somatically rearranged regions may comprise nucleic acids from developing or from fully developed lymphocytes, where developing lymphocytes are cells in which rearrangement of immune genes has not been completed to form molecules having full V(D)J regions. Exemplary incomplete somatically rearranged regions include incomplete IgH molecules (such as, molecules containing only D-J regions), incomplete TCR$\delta$ molecules (such as, molecules containing only D-J regions), and inactive IgK (for example, comprising Kde-V regions).

Adequate sampling of the cells is an important aspect of interpreting the repertoire data, as described further below in the definitions of "clonotype" and "repertoire." For example, starting with 1,000 cells creates a minimum frequency that the assay is sensitive to regardless of how many sequencing reads are obtained. Therefore one aspect of this invention is the development of methods to quantitate the number of input immune receptor molecules. This has been implemented this for TCR$\beta$ and IgH sequences. In either case the same set of primers are used that are capable of amplifying all the different sequences. In order to obtain an absolute number of copies, a real time PCR with the multiplex of primers is performed along with a standard with a known number of immune receptor copies. This real time PCR measurement can be made from the amplification reaction that will subsequently be sequenced or can be done on a separate aliquot of the same sample. In the case of DNA, the absolute number of rearranged immune receptor molecules can be readily converted to number of cells (within 2 fold as some cells will have 2 rearranged copies of the specific immune receptor assessed and others will have one). In the case of cDNA the measured total number of rearranged molecules in the real time sample can be extrapolated to define the total number of these molecules used in another amplification reaction of the same sample. In addition, this method can be combined with a method to determine the total amount of RNA to define the number of rearranged immune receptor molecules in a unit amount (say 1 µg) of RNA assuming a specific efficiency of cDNA synthesis. If the total amount of cDNA is measured then the efficiency of cDNA synthesis need not be considered. If the number of cells is also known then the rearranged immune receptor copies per cell can be computed. If the number of cells is not known, one can estimate it from the total RNA as cells of specific type usually generate comparable amount of RNA. Therefore from the copies of rearranged immune receptor molecules per 1 µg one can estimate the number of these molecules per cell.

One disadvantage of doing a separate real time PCR from the reaction that would be processed for sequencing is that there might be inhibitory effects that are different in the real time PCR from the other traction as different enzymes, input DNA, and other conditions may be utilized. Processing the products of the real time PCR for sequencing would ameliorate this problem. However low copy number using real time PCR can be due to either low number of copies or to inhibitory effects, or other suboptimal conditions in the reaction.

Another approach that can be utilized is to add a known amount of unique immune receptor rearranged molecules with a known sequence, i.e. known amounts of one or more internal standards, to the cDNA or genomic DNA from a sample of unknown quantity. By counting the relative number of molecules that are obtained for the known added sequence compared to the rest of the sequences of the same sample, one can estimate the number of rearranged immune receptor molecules in the initial cDNA sample. (Such techniques for molecular counting are well-known, e.g. Brenner et al, U.S. Pat. No. 7,537,897, which is incorporated herein by reference). Data from sequencing the added unique sequence can be used to distinguish the different possibilities if a real time PCR calibration is being used as well. Low copy number of rearranged immune receptor in the DNA (or cDNA) would create a high ratio between the number of molecules for the spiked sequence compared to the rest of the sample sequences. On the other hand, if the measured low copy number by real time PCR is due to inefficiency in the reaction, the ratio would not be high.

Amplification of Nucleic Acid Populations

As noted below, amplicons of target populations of nucleic acids may be generated by a variety of amplification techniques. In one aspect of the invention, multiplex PCR is used to amplify members of a mixture of nucleic acids, particularly mixtures comprising recombined immune molecules such as T cell receptors. B cell receptors, or portions thereof. Guidance for carrying out multiplex PCRs of such immune molecules is found in the following references, which are incorporated by reference: Morley, U.S. Pat. No. 5,296,351; Gorski, U.S. Pat. No. 5,837,447; Dau, U.S. Pat. No. 6,087,096; Von Dongen et al, U.S. patent publication 2006/0234234; European patent publication EP 1544308B1; and the like. The foregoing references describe the technique referred to as "spectratyping," where a population of immune molecules are amplified by multiplex PCR after which the sequences of the resulting amplicon are physically separated, e.g. by electrophoresis, in order to determine whether there is a predominant size class. Such a class would indicate a predominant clonal population of lymphocytes which, in turn, would be indicative of disease state. In spectratyping, it is important to select primers that display little or no cross-reactivity (i.e. that do not anneal to binding sites of other primers); otherwise there may be a false representation of size classes in the amplicon. In the present invention, so long as the nucleic acids of a population are uniformly amplified, cross-reactivity of primers is permissible because the sequences of the amplified nucleic acids are analyzed in the present invention, not merely their sizes. As described more fully below, in one aspect, the step of spatially isolating individual nucleic acid molecules is achieved by carrying out a primary multiplex amplification of a preselected somatically rearranged region or portion thereof (i.e. target sequences) using forward and reverse primers that each have tails non-complementary to the target sequences to produce a first amplicon whose member sequences have common sequences at each end that allow further manipulation. For example, such common ends may include primer binding sites for continued amplification using just a single forward primer and a single reverse primer instead of multiples of each, or for bridge amplification of Individual molecules on a solid surface, or the like. Such common ends may be added in a single amplification as described above, or they may be added in a two-step procedure to avoid difficulties associated with manufacturing and exercising quality control over mixtures of long primers (e.g. 50-70 bases or more). In such a two-step process (described more fully below and illustrated in FIGS. 4A-4B), the primary amplification is carried out as described above, except that the primer tails are limited in length to provide only forward and reverse primer binding sites at the ends of the sequences of the first amplicon. A secondary amplification is then carried out using secondary amplification primers specific to these primer binding sites to add further sequences to the ends of a second amplicon. The secondary amplification primers have tails non-complementary to the target sequences, which form the ends of the second amplicon and which may be used in connection with sequencing the clonotypes of the second amplicon. In one embodiment, such added sequences may include primer binding sites for generating sequence reads and primer binding sites for carrying out bridge PCR on a solid surface to generate clonal populations of spatially isolated individual molecules, for example, when Solexa-based sequencing is used. In this latter approach, a sample of sequences from the second amplicon are disposed on a solid surface that has attached complementary oligonucleotides capable of annealing to sequences of the sample, after which cycles of primer extension, denaturation, annealing are implemented until clonal populations of templates are formed. Preferably, the size of the sample is selected so that (i) it includes an effective representation of clonotypes in the original sample, and (ii) the density of clonal populations on the solid surface is in a range that permits unambiguous sequence determination of clonotypes.

TCR or BCR sequences or portions thereof can be amplified from nucleic acid in a multiplex reaction using at least one primer that annals to the C region and one or more primers that can anneal to one or more V segments (as illustrated in FIGS. 2A-2B and FIGS. 4A-4B and discussed more fully below). The region to be amplified can include the full clonal sequence or a subset of the clonal sequence, including the V-D junction, D-J junction of an immunoglobulin or T-cell receptor gene, the full variable region of an immunoglobulin or T-cell receptor gene, the antigen recognition region, or a CDR, e.g., complementarity determining region 3 (CDR3).

Figure 3A:
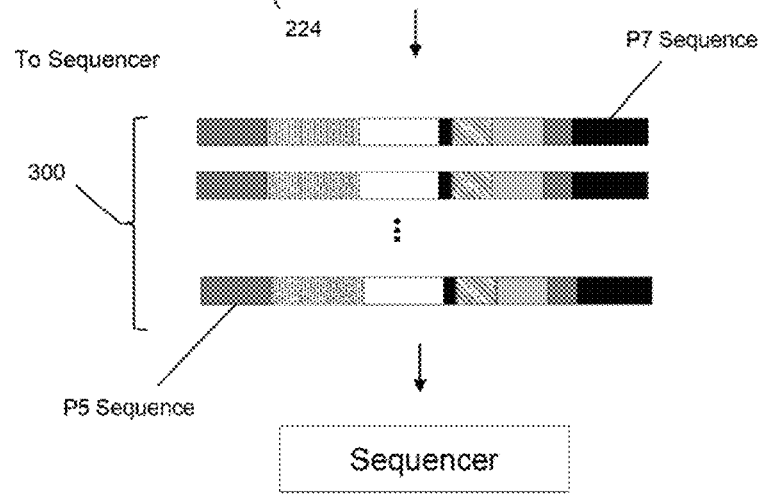
FIG. 3A illustrates a PCR product to be sequenced that was amplified using the scheme of FIGS. 2A-2B.
Figure 3B:
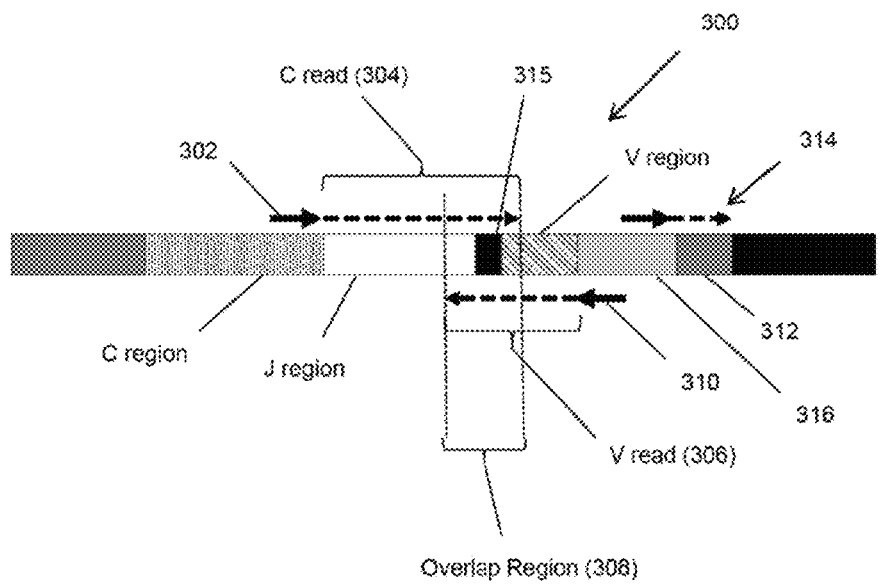
FIG. 3B illustrates details of determining a nucleotide sequence of the PCR product of FIG. 3A.

The TCR or immunoglobulin sequence can amplified using a primary and a secondary amplification step. Each of the different amplification steps can comprise different primers. The different primers can introduce sequence not originally present in the immune gene sequence. For example, the amplification procedure can add new primer binding sites to the ends of the target sequences to convert a multiplex amplification to a singleplex amplification or the amplification procedure can add one or more tags to the 5' and/or 3' and of amplified TCR or immunoglobulin sequence (as illustrated in FIGS. 3A-3B). The tag can be sequence that facilitates subsequent sequencing of the amplified DNA. The tag can be sequence that facilitates binding the amplified sequence to a solid support.

After amplification of DNA from the genome (or amplification of nucleic acid in the form of cDNA by reverse transcribing RNA), the individual nucleic acid molecules can be isolated, optionally re-amplified, and then sequenced individually. Exemplary amplification protocols may be found in van Dongen et al, Leukemia, 17: 2257-2317 (2003) or van Dongen et al. U.S. patent publication 2006/0234234, which is incorporated by reference. Briefly, an exemplary protocol is as follows: Reaction buffer ABI Buffer II or ABI Gold Buffer (Life Technologies. San Diego, Calif.); 50 µL final reaction volume 100 ng sample DNA; 10 pmol of each primer (subject to adjustments to balance amplification as described below); dNTPs at 200 µM final concentration; $MgCl_2$ at 1.5 mM final concentration (subject to optimization depending on target sequences and polymerase); Taq polymerase (1-2 U/tube); cycling conditions: preactivation 7 min at 95° C.; annealing at 60° C.; cycling times: 30 s denaturation; 30 s annealing; 30 s extension. Polymerases that can be used for amplification in the methods of the invention are commercially available and include, for example. Taq polymerase. AccuPrime polymerase, or Pfu. The choice of polymerase to use can be based on whether fidelity or efficiency is preferred.

Methods for isolation of nucleic acids from a pool include subcloning nucleic acid into DNA vectors and transforming bacteria (bacterial cloning), spatial separation of the molecules in two dimensions on a solid substrate (e.g., glass slide), spatial separation of the molecules in three dimensions in a solution within micelles (such as can be achieved using oil emulsions with or without immobilizing the molecules on a solid surface such as beads), or using microreaction chambers in, for example, microfluidic or nano-fluidic chips. Dilution can be used to ensure that on average a single molecule is present in a given volume, spatial region, bead, or reaction chamber. Guidance for such methods of isolating individual nucleic acid molecules is found in the following references: Sambrook, Molecular Cloning: A Laboratory Manual (Cold Spring Harbor Laboratory Press, 2001s); Shendure et al, Science, 309: 1728-1732 (including supplemental material) (2005); U.S. Pat. No. 6,300,070; Bentley et al, Nature, 456:

53-59 (including supplemental material) (2008); U.S. Pat. No. 7,323,305; Matsubara et al, Biosensors & Bioelectronics, 20: 1482-1490 (2005); U.S. Pat. No. 6,753,147; and the like.

Real time PCR, picogreen staining, nanofluidic electrophoresis (e.g. LabChip) or UV absorption measurements can be used in an initial step to judge the functional amount of amplifiable material.

In one aspect, multiplex amplifications are carried out so that relative amounts of sequences in a starting population are substantially the same as those in the amplified population, or amplicon. That is, multiplex amplifications are carried out with minimal amplification bias among member sequences of a sample population. In one embodiment, such relative amounts are substantially the same if each relative amount in an amplicon is within five fold of its value in the starting sample. In another embodiment, such relative amounts are substantially the same if each relative amount in an amplicon is within two fold of its value in the starting sample. As discussed more fully below, amplification bias in PCR may be detected and corrected using conventional techniques so that a set of PCR primers may be selected for a predetermined repertoire that provide unbiased amplification of any sample.

In regard to many repertoires based on TCR or BCR sequences, a multiplex amplification optionally uses all the V segments. The reaction is optimized to attempt to get amplification that maintains the relative abundance of the sequences amplified by different V segment primers. Some of the primers are related, and hence many of the primers may "cross talk," amplifying templates that are not perfectly matched with it. The conditions are optimized so that each template can be amplified in a similar fashion irrespective of which primer amplified it. In other words if there are two templates, then after 1,000 fold amplification both templates can be amplified approximately 1,000 fold, and it does not matter that for one of the templates half of the amplified products carried a different primer because of the cross talk. In subsequent analysis of the sequencing data the primer sequence is eliminated from the analysis, and hence it does not matter what primer is used in the amplification as long as the templates are amplified equally.

Figure 2A:
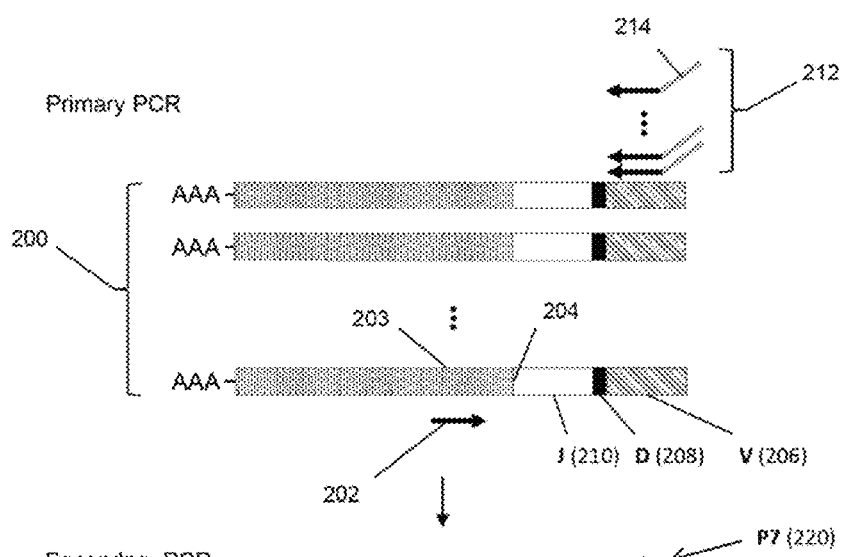
FIGS. 2A-2B show a two-staged PCR scheme for amplifying TCRβ genes.
Figure 2B:
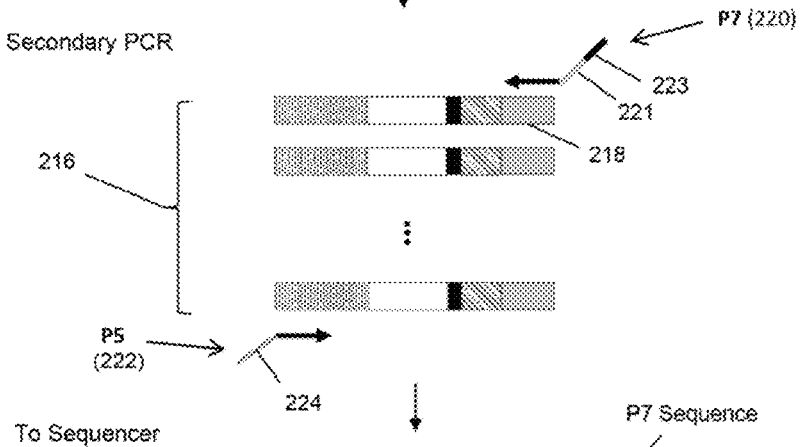

In one embodiment, amplification bias may be avoided by carrying out a two-stage amplification (as illustrated in FIGS. 2A-2B) wherein a small number of amplification cycles are implemented in a first, or primary, stage using primers having tails non-complementary with the target sequences. The tails include primer binding sites that are added to the ends of the sequences of the primary amplicon so that such sites are used in a second stage amplification using only a single forward primer and a single reverse primer, thereby eliminating a primary cause of amplification bias. Preferably, the primary PCR will have a small enough number of cycles (e.g. 5-10) to minimize the differential amplification by the different primers. The secondary amplification is done with one pair of primers and hence the issue of differential amplification is minimal. One percent of the primary PCR is taken directly to the secondary PCR. Thirty-five cycles (equivalent to ~28 cycles without the 100 fold dilution step) used between the two amplifications were sufficient to show a robust amplification irrespective of whether the breakdown of cycles were: one cycle primary and 34 secondary or 25 primary and 10 secondary. Even though ideally doing only 1 cycle in the primary PCR may decrease the amplification bias, there are other considerations. One aspect of this is representation. This plays a role when the starting input amount is not in excess to the number of reads ultimately obtained. For example, if 1,000,000 reads are obtained and starting with 1,000,000 input molecules then taking only representation from 100,000 molecules to the secondary amplification would degrade the precision of estimating the relative abundance of the different species in the original sample. The 100 fold dilution between the 2 steps means that the representation is reduced unless the primary PCR amplification generated significantly more than 100 molecules. This indicates that a minimum 8 cycles (256 fold), but more comfortably 10 cycle (~1,000 fold), may be used. The alternative to that is to take more than 1% of the primary PCR into the secondary but because of the high concentration of primer used in the primary PCR, a big dilution factor is can be used to ensure these primers do not interfere in the amplification and worsen the amplification bias between sequences. Another alternative is to add a purification or enzymatic step to eliminate the primers from the primary PCR to allow a smaller dilution of it. In this example, the primary PCR was 10 cycles and the second 25 cycles.

Generating Sequence Reads for Clonotypes

Any high-throughput technique for sequencing nucleic acids can be used in the method of the invention. Preferably, such technique has a capability of generating in a cost-effective manner a volume of sequence data from which at least 1000 clonotypes can be determined, and preferably, from which at least 10,000 to 1,000,000 clonotypes can be determined. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of the separated molecules has more recently been demonstrated by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel. These sequencing approaches can thus be used to study the repertoire of T-cell receptor (TCR) and/or B-cell receptor (BCR). In one aspect of the invention, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et at Nature, 456: 53-59 (2008) or Complete Genomics sequencing, e.g. Drmanac et al. Science, 327: 78-81 (2010)), arrays of wells, which may include bead- or particle-bound templates (such as with 454, e.g. Margulies et al, Nature, 437: 376-380 (2005) or Ion Torrent sequencing. U.S. patent publication 2010/0137143 or 2010/0304982), micromachined membranes (such as with SMRT sequencing. e.g. Eid et al, Science, 323: 133-138 (2009)), or bead arrays (as with SOLiD sequencing or polony sequencing, e.g. Kim et al, Science, 316: 1481-1414 (2007)). In another aspect, such methods comprise amplifying the isolated molecules either before or after they are spatially isolated on a solid surface. Prior amplification may comprise emulsion-based amplification, such as emulsion PCR, or rolling circle amplification. Of particular interest is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina. Inc., San Diego, Calif., 2010); and further in the following references: U.S. Pat. Nos. 6,090,592; 6,300,070; 7,115,400; and EP0972081B1; which are incorporated by reference. In one embodiment, individual molecules disposed and amplified on a solid surface form clusters in a density of at least $10^5$ clusters per $cm^2$; or in a density of at least $5 \times 10^5$ per $cm^2$; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

In one aspect, a sequence-based clonotype profile of an individual is obtained using the following steps: (a) obtaining a nucleic acid sample from T-cells and/or B-cells of the individual; (b) spatially isolating individual molecules derived from such nucleic acid sample, the individual molecules comprising at least one template generated from a nucleic acid in the sample, which template comprises a somatically rearranged region or a portion thereof, each individual molecule being capable of producing at least one sequence read; (c) sequencing said spatially isolated individual molecules; and (d) determining abundances of different sequences of the nucleic acid molecules from the nucleic; and sample to generate the clonotype profile. In one embodiment, each of the somatically rearranged regions comprise a V region and a J region. In another embodiment, the step of sequencing comprises bidirectionally sequencing each of the spatially isolated individual molecules to produce at least one forward sequence read and at least one reverse sequence read. Further to the latter embodiment, at least one of the forward sequence reads and at least one of the reverse sequence reads have an overlap region such that bases of such overlap region are determined by a reverse complementary relationship between such sequence reads. In still another embodiment, each of the somatically rearranged regions comprise a V region and a J region and the step of sequencing further includes determining a sequence of each of the individual nucleic acid molecules from one or more of its forward sequence reads and at least one reverse sequence read starting from a position in a J region and extending in the direction of its associated V region. In another embodiment, individual molecules comprise nucleic acids selected from the group consisting of complete IgH molecules, incomplete IgH molecules, complete IgK complete, IgK inactive molecules. TCRβ molecules. TCRγ molecules, complete TCRδ molecules, and incomplete TCRδ molecules. In another embodiment, the step of sequencing comprises generating the sequence reads having monotonically decreasing quality scores. Further to the latter embodiment, monotonically decreasing quality scores are such that the sequence reads have error rates no better than the following: 0.2 percent of sequence reads contain at least one error in base positions 1 to 50, 0.2 to 1.0 percent of sequence reads contain at least one error in positions 51-75, 0.5 to 1.5 percent of sequence reads contain at least one error in positions 76-100. In another embodiment, the above method comprises the following steps: (a) obtaining a nucleic acid sample from T-cells and/or B-cells of the individual; (b) spatially isolating individual molecules derived from such nucleic acid sample, the individual molecules comprising nested sets of templates each generated from a nucleic acid in the sample and each containing a somatically rearranged region or a portion thereof, each nested set being capable of producing a plurality of sequence reads each extending in the same direction and each starting from a different position on the nucleic acid from which the nested set was generated; (c) sequencing said spatially isolated individual molecules; and (d) determining abundances of different sequences of the nucleic acid molecules from the nucleic acid sample to generate the clonotype profile. In one embodiment, the step of sequencing includes producing a plurality of sequence reads for each of the nested sets. In another embodiment, each of the somatically rearranged regions comprise a V region and a J region, and each of the plurality of sequence reads starts from a different position in the V region and extends in the direction of its associated J region.

In one aspect, for each sample from an individual, the sequencing technique used in the methods of the invention generates sequences of least 1000 clonotypes per run; in another aspect, such technique generates sequences of at least 10,000 clonotypes per run; in another aspect, such technique generates sequences of at least 100,000 clonotypes per run; in another aspect, such technique generates sequences of at least 500,000 clonotypes per run; and in another aspect, such technique generates sequences of at least 1,000,000 clonotypes per run. In still another aspect, such technique generates sequences of between 100,000 to 1,000,000 clonotypes per run per individual sample.

The sequencing technique used in the methods of the provided invention can generate about 30 bp, about 40 bp, about 50 bp, about 60 bp, about 70 bp, about 80 bp, about 90 bp, about 100 bp, about 110, about 120 bp per read, about 150 bp, about 200 bp, about 250 bp, about 300 bp, about 350 bp, about 400 bp, about 450 bp, about 500 bp, about 550 bp, or about 600 bp per read.

Clonotype Determination from Sequence Data

Figure 4A:
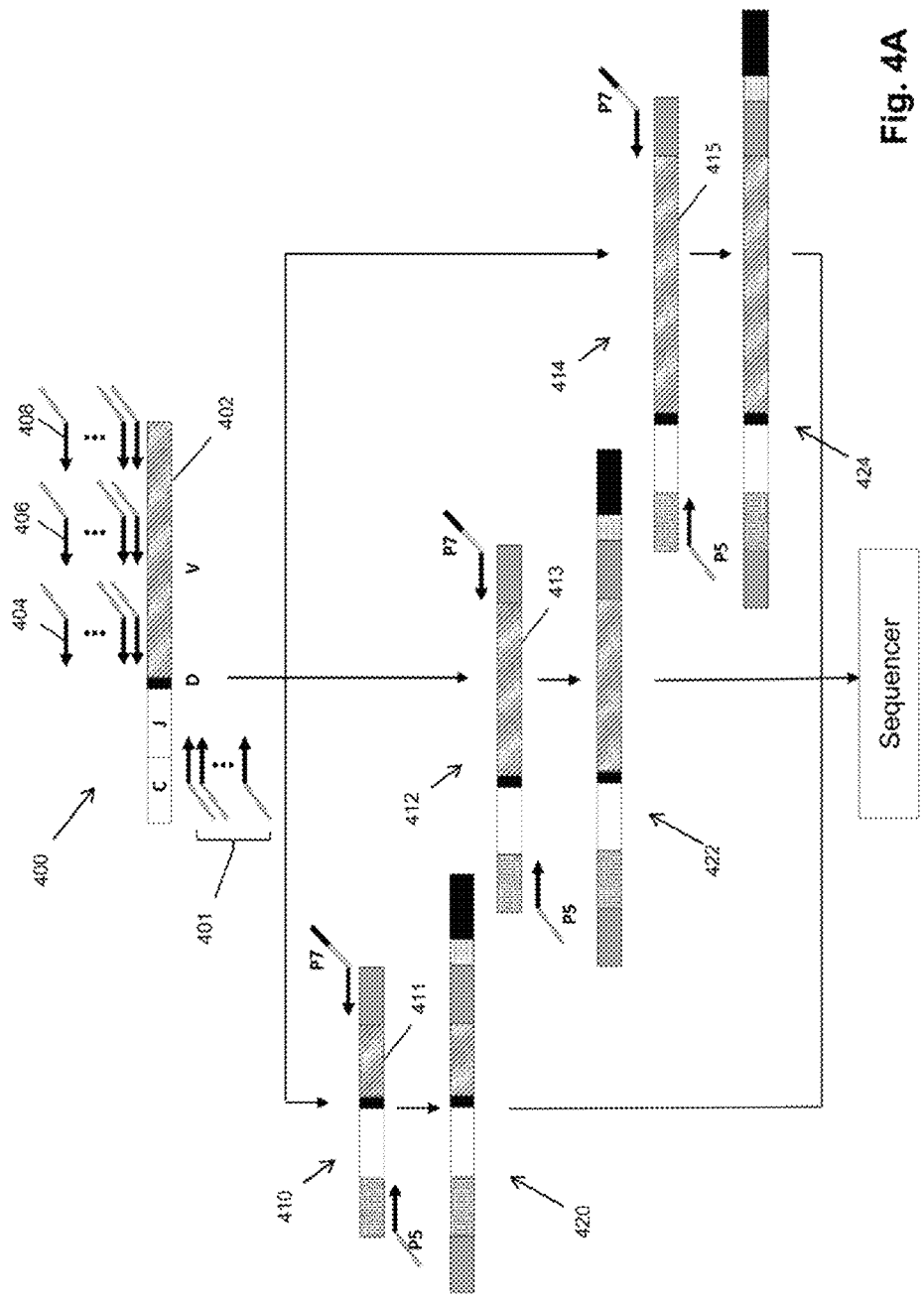
FIG. 4A illustrates a PCR scheme for generating three sequencing templates from an IgH chain in a single reaction.
Figure 4B:
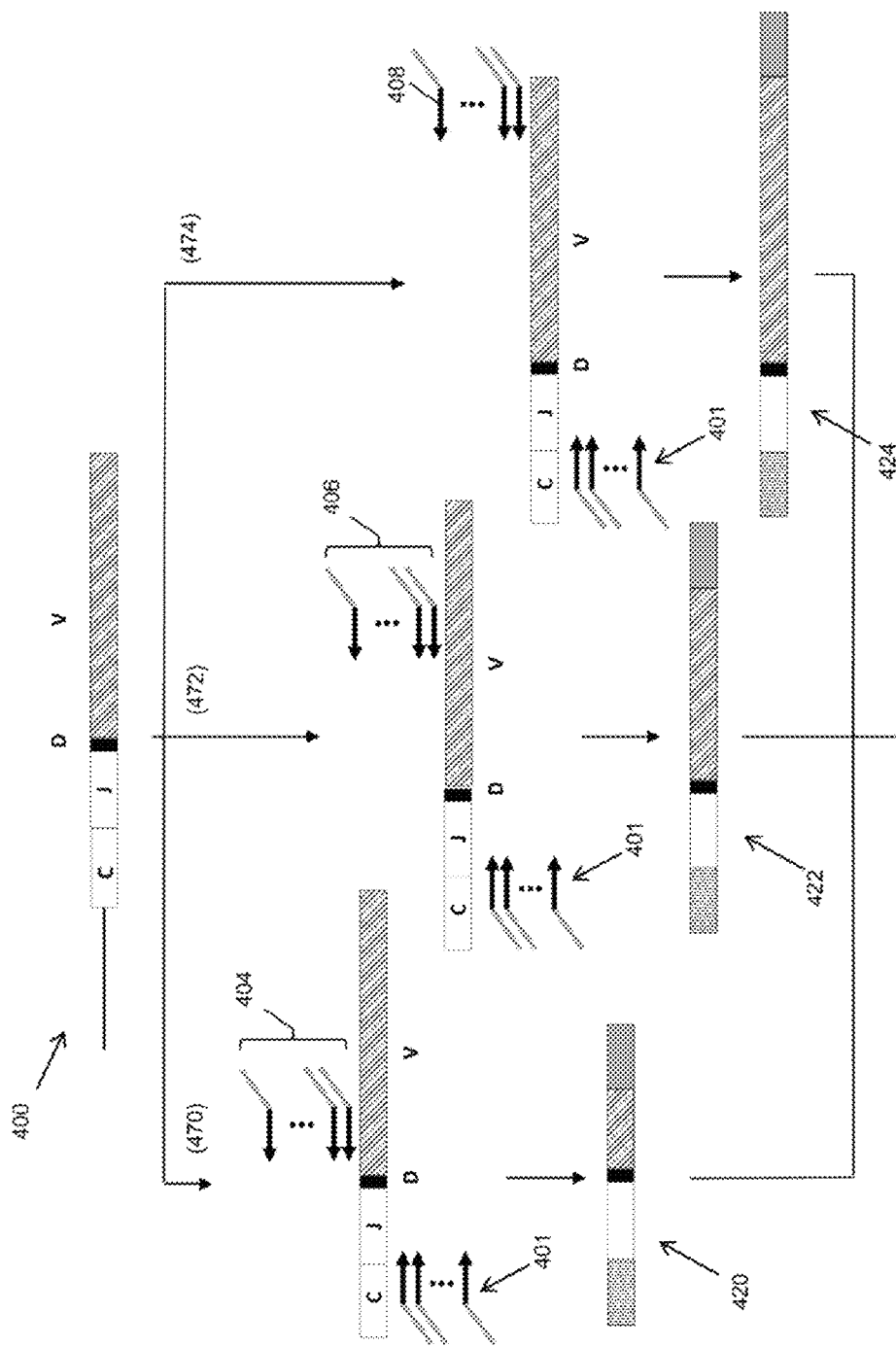
FIGS. 4B-4C illustrates a PCR scheme for generating three sequencing templates from an IgH chain in three separate reactions after which the resulting amplicons are combined for a secondary PCR to add P5 and P7 primer binding sites.
Figure 4C:
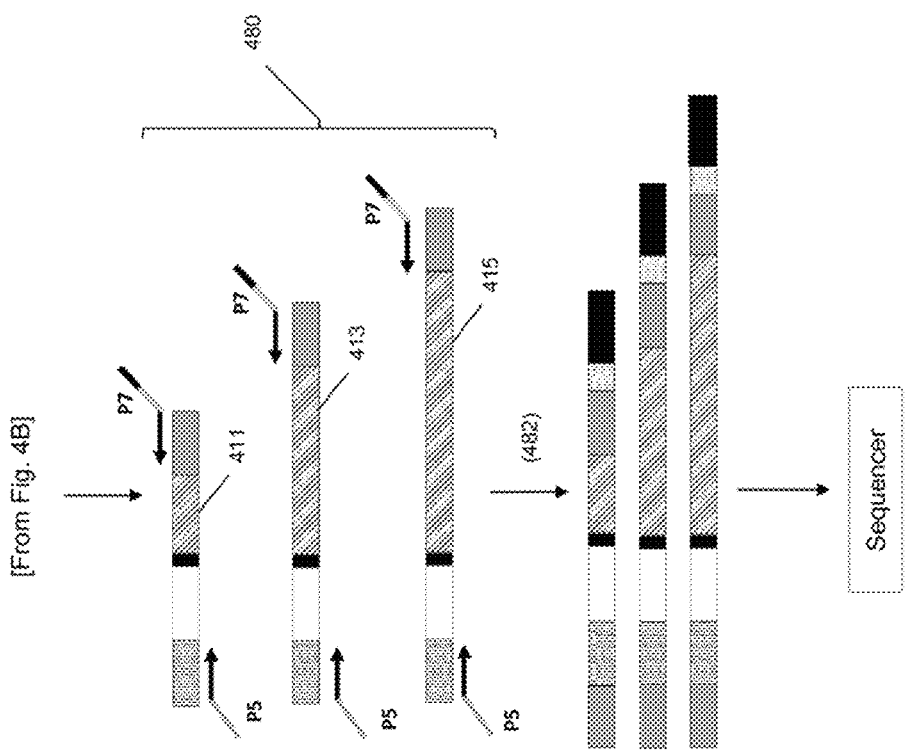

In one aspect of the invention, sequences of clonotypes (including but not limited to those derived from IgH, TCRα, TCRβ, TCRγ, TCRδ, and/or IgLκ (IgK)) may be determined by combining information from one or more sequence reads, for example, along the V(D)J regions of the selected chains. In another aspect, sequences of clonotypes are determined by combining information from a plurality of sequence reads. Such pluralities of sequence reads may include one or more sequence reads along a sense strand (i.e. "forward" sequence reads) and one or more sequence reads along its complementary strand (i.e. "reverse" sequence reads). When multiple sequence reads are generated along the same strand, separate templates are first generated by amplifying sample molecules with primers selected for the different positions of the sequence reads. This concept is illustrated in FIG. 4A where primers (404, 406 and 408) are employed to generate amplicons (410, 412, and 414, respectively) in a single reaction. Such amplifications may be carried out in the same reaction or in separate reactions. In one aspect, whenever PCR is employed, separate amplification reactions are used for generating the separate templates which, in turn, are combined and used to generate multiple sequence reads along the same strand. This latter approach is preferable for avoiding the need to balance primer concentrations (and/or other reaction parameters) to ensure equal amplification of the multiple templates (sometimes referred to herein as "balanced amplification" or "unbias amplification"). The generation of templates in separate reactions is illustrated in FIGS. 4B-C. There a sample containing IgH (400) is divided into three portions (472, 474, and 476) which are added to separate PCRs using J region primers (401) and V region primers (404, 406, and 408, respectively) to produce amplicons (420, 422 and 424, respectively). The latter amplicons are then combined (478) in secondary PCR (480) using P5 and P7 primers to prepare the templates (482) for bridge PCR and sequencing on an Illumina GA sequencer, or like instrument.

Sequence reads of the invention may have a wide variety of lengths, depending in part on the sequencing technique being employed. For example, for some techniques, several trade-offs may arise in its implementation, for example, (i) the number and lengths of sequence reads per template and (ii) the cost and duration of a sequencing operation. In one embodiment, sequence reads are in the range of from 20 to 400 nucleotides; in another embodiment, sequence reads are in a range of from 30 to 200 nucleotides; in still another embodiment, sequence reads are in the range of from 30 to 120 nucleotides. In one embodiment, 1 to 4 sequence reads are generated for determining the sequence of each clonotype; in another embodiment, 2 to 4 sequence reads are generated for determining the sequence of each clonotype; and in another embodiment, 2 to 3 sequence reads are generated for determining the sequence of each clonotype. In the foregoing embodiments, the numbers given are exclusive of sequence reads used to identify samples from different individuals. The lengths of the various sequence reads used in the embodiments described below may also vary based on the information that is sought to be captured by the read; for example, the starting location and length of a sequence read may be designed to provide the length of an NDN region as well as its nucleotide sequence: thus, sequence reads spanning the entire NDN region are selected. In other aspects, one or more sequence reads that in combination (but not separately) encompass a D and/or NDN region are sufficient.

In another aspect of the invention, sequences of clonotypes are determined in part by aligning sequence reads to one or more V region reference sequences and one or more J region reference sequences, and in part by base determination without alignment to reference sequences, such as in the highly variable NDN region. A variety of alignment algorithms may be applied to the sequence reads and reference sequences. For example, guidance for selecting alignment methods is available in Batzoglou, Briefings in Bioinformatics, 6: 6-22 (2005), which is incorporated by reference. In one aspect, whenever V reads or C reads (as mentioned above) are aligned to V and J region reference sequences, a tree search algorithm is employed, e.g. as described generally in Gusfield (cited above) and Cormen et al, Introduction to Algorithms, Third Edition (The MIT Press, 2009).

Figure 3C:
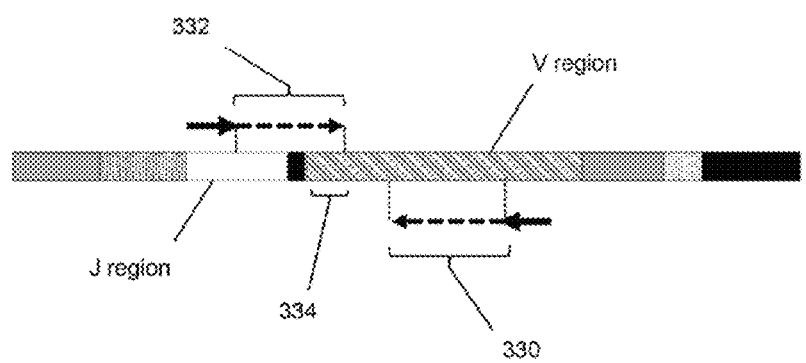
FIG. 3C illustrates details of another embodiment of determining a nucleotide sequence of the PCR product of FIG. 3A.

In another aspect, an end of at least one forward read and an end of at least one reverse read overlap in an overlap region (e.g. 308 in FIG. 3B), so that the bases of the reads are in a reverse complementary relationship with one another. Thus, for example, if a forward read in the overlap region is "5'-acgttgc", then a reverse read in a reverse complementary relationship is "5'-gcaacgt" within the same overlap region. In one aspect, bases within such an overlap region are determined, at least in part, from such a reverse complementary relationship. That is, a likelihood of a base call (or a related quality score) in a prospective overlap region is increased if it preserves, or is consistent with, a reverse complementary relationship between the two sequence reads. In one aspect, clonotypes of TCRβ and IgH chains (illustrated in FIG. 3B) are determined by at least one sequence read starting in its J region and extending in the direction of its associated V region (referred to herein as a "C read" (304)) and at least one sequence read starting in its V region and extending in the direction of its associated J region (referred to herein as a "V read" (306)). Overlap region (308) may or may not encompass the NDN region (315) as shown in FIG. 3B. Overlap region (30) may be entirely in the J region, entirely in the NDN region, entirely in the V region, or it may encompass a J region-NDN region boundary or a V region-NDN region boundary, or both such boundaries (as illustrated in FIG. 3B). Typically, such sequence reads are generated by extending sequencing primers. e.g. (302) and (310) in FIG. 3B, with a polymerase in a sequencing-by-synthesis reaction, e.g. Metzger, Nature Reviews Genetics, 11: 31-46 (2010); Fuller et al, Nature Biotechnology, 27: 1013-1023 (2009). The binding sites for primers (302) and (310) are predetermined, so that they can provide a starting point or anchoring point for initial alignment and analysis of the sequence reads. In one embodiment, a C read is positioned so that it encompasses the D and/or NDN region of the TCRβ or IgH chain and includes a portion of the adjacent V region, e.g. as illustrated in FIGS. 3B and 3C. In one aspect, the overlap of the V read and the C read in the V region is used to align the reads with one another. In other embodiments, such alignment of sequence reads is not necessary. e.g. with TCRβ chains, so that a V read may only be long enough to identify the particular V region of a clonotype. This latter aspect is illustrated in FIG. 3C. Sequence read (330) is used to identify a V region, with or without overlapping another sequence read, and another sequence read (332) traverses the NDN region and is used to determine the sequence thereof. Portion (334) of sequence read (332) that extends into the V region is used to associate the sequence information of sequence read (332) with that of sequence read (330) to determine a clonotype. For some sequencing methods, such as base-by-base approaches like the Solexa sequencing method, sequencing run time and reagent costs are reduced by minimizing the number of sequencing cycles in an analysis. Optionally, as illustrated in FIG. 3B, amplicon (300) is produced with sample tag (312) to distinguish between clonotypes originating from different biological samples, e.g. different patients. Sample tag (312) may be identified by annealing a primer to primer binding region (316) and extending it (314) to produce a sequence read across tag (312), from which sample tag (312) is decoded.

The IgH chain is more challenging to analyze than TCRβ chain because of at least two factors: i) the presence of somatic mutations makes the mapping or alignment more difficult, and ii) the NDN region is larger so that it is often not possible to map a portion of the V segment to the C read. In one aspect of the invention, this problem is overcome by using a plurality of primer sets for generating V reads, which are located at different locations along the V region, preferably so that the primer binding sites are nonoverlapping and spaced apart, and with at least one primer binding site adjacent to the NDN region, e.g. in one embodiment from 5 to 50 bases from the V-NDN junction, or in another embodiment from 10 to 50 bases from the V-NDN junction. The redundancy of a plurality of primer sets minimizes the risk of failing to detect a clonotype due to a failure of one or two primers having binding sites affected by somatic mutations. In addition, the presence of at least one primer binding site adjacent to the NDN region makes it more likely that a V read will overlap with the C read and hence effectively extend the length of the C read. This allows for the generation of a continuous sequence that spans all sizes of NDN regions and that can also map substantially the entire V and J regions on both sides of the NDN region. Embodiments for carrying out such a scheme are illustrated in FIGS. 4A and 4D. In FIG. 4A, a sample comprising IgH chains (400) are sequenced by generating a plurality amplicons for each chain by amplifying the chains with a single set of J region primers (401) and a plurality (three shown) of sets of V region (402) primers (404, 406, 408) to produce a plurality of nested amplicons (e.g., 410, 412, 416) all comprising the same NDN region and having different lengths encompassing successively larger portions (411, 413, 415) of V region (402). Members of a nested set may be grouped together after sequencing by noting the identify (or substantial identity) of their respective NDN, J and/or C regions, thereby allowing reconstruction of a longer V(D)J segment than would be the case otherwise for a sequencing platform with limited read length and/or sequence quality. In one embodiment, the plurality of primer sets may be a number in the range of from 2 to 5. In another embodiment the plurality is 2-3; and still another embodiment the plurality is 3. The concentrations and positions of the primers in a plurality may vary widely. Concentrations of the V region primers may or may not be the same. In one embodiment, the primer closest to the NDN region has a higher concentration than the other primers of the plurality, e.g. to insure that amplicons containing the NDN region are represented in the resulting amplicon. In a particular embodiment where a plurality of three primers is employed, a concentration ratio of 60:20:20 is used. One or more primers (e.g. 435 and 437 in FIG. 4B) adjacent to the NDN region (444) may be used to generate one or more sequence reads (e.g. 434 and 436) that overlap the sequence read (442) generated by J region primer (432), thereby improving the quality of base calls in overlap region (140). Sequence reads from the plurality of primers may or may not overlap the adjacent downstream primer binding site and/or adjacent downstream sequence read. In one embodiment, sequence reads proximal to the NDN region (e.g. 436 and 438) may be used to identify the particular V region associated with the clonotype. Such a plurality of primers reduces the likelihood of incomplete or failed amplification in case one of the primer binding sites is hypermutated during immunoglobulin development. It also increases the likelihood that diversity introduced by hypermutation of the V region will be capture in a clonotype sequence. A secondary PCR may be performed to prepare the nested amplicons for sequencing, e.g. by amplifying with the P5 (401) and P7 (404, 406, 408) primers as illustrated to produce amplicons (420, 422, and 424), which may be distributed as single molecules on a solid surface, where they are further amplified by bridge PCR, or like technique.

Base calling in NDN regions (particularly of IgH chains) can be improved by using the codon structure of the flanking J and V regions, as illustrated in FIG. 4E. (As used herein, "codon structure" means the codons of the natural reading frame of segments of TCR or BCR transcripts or genes outside of the NDN regions, e.g. the V region, J region, or the like.) There amplicon (450), which is an enlarged view of the amplicon of FIG. 4B, is shown along with the relative positions of C read (442) and adjacent V read (434) above and the codon structures (452 and 454) of V region (430) and J region (446), respectively, below. In accordance with this aspect of the invention, after the codon structures (452 and 454) are identified by conventional alignment to the V and J reference sequences, bases in NDN region (456) are called (or identified) one base at a time moving from J region (446) toward V region (430) and in the opposite direction from V region (430) toward J region (446) using sequence reads (434) and (442). Under normal biological conditions, only the recombined TCR or IgH sequences that have in frame codons from the V region through the NDN region and to the J region are expressed as proteins. That is, of the variants generated somatically only ones expressed are those whose J region and V region codon frames are in-frame with one another and remain in-frame through the NDN region. (Here the correct frames of the V and J regions are determined from reference sequences). If an out-of-frame sequence is identified based one or more low quality base calls, the corresponding clonotype is flagged for re-evaluation or as a potential disease-related anomaly. If the sequence identified is in-frame and based on high quality base calls, then there is greater confidence that the corresponding clonotype has been correctly called. Accordingly, in one aspect, the invention includes a method of determining V(D)J-based clonotypes from bidirectional sequence reads comprising the steps of (a) generating at least one J region sequence read that begins in a J region and extends into an NDN region and at least one V region sequence read that begins in the V regions and extends toward the NDN region such that the J region sequence read and the V region sequence read are overlapping in an overlap region, and the J region and the V region each have a codon structure; (b) determining whether the codon structure of the J region extended into the NDN region is in frame with the codon structure of the V region extended toward the NDN region. In a further embodiment, the step of generating includes generating at least one V region sequence read that begins in the V region and extends though the NDN region to the J region, such that the J region sequence read and the V region sequence read are overlapping in an overlap region.

Somatic Hypermutations. In one embodiment, IgH-based clonotypes that have undergone somatic hypermutation are determined as follows. A somatic mutation is defined as a sequenced base that is different from the corresponding base of a reference sequence (of the relevant segment, usually V, J or C) and that is present in a statistically significant number of reads. In one embodiment, C reads may be used to find somatic mutations with respect to the mapped J segment and likewise V reads for the V segment. Only pieces or the C and V reads are used that are either directly mapped to J or V segments or that are inside the clonotype extension up to the NDN boundary. In this way, the NDN region is avoided and the same 'sequence information' is not used for mutation finding that was previously used for clonotype determination (to avoid erroneously classifying as mutations nucleotides that are really just different recombined NDN regions). For each segment type, the mapped segment (major allele) is used as a scaffold and all reads are considered which have mapped to this allele during the read mapping phase. Each position of the reference sequences where at least one read has mapped is analyzed for somatic mutations. In one embodiment, the criteria for accepting a non-reference base as a valid mutation include the following: 1) at least N reads with the given mutation base, 2) at least a given fraction N/M reads (where M is the total number of mapped reads at this base position) and 3) a statistical cut based on the binomial distribution, the average Q score of the N reads at the mutation base as well as the number (M-N) of reads with a non-mutation base. Preferably, the above parameters are selected so that the false discovery rate of mutations per clonotype is less than 1 in 1000, and more preferably, less than 1 in 10000.

Phylogenic Clonotypes (Clans). In cancers, such as lymphoid neoplasms, a single lymphocyte progenitor may give rise to many related lymphocyte progeny, each possessing and/or expressing a slightly different TCR or BCR, and therefore a different clonotype, due to cancer-related somatic mutation(s), such as base substitutions, aberrant rearrangements, or the like. Cells producing such clonotypes are referred to herein as phylogenic clones, and a set of such related clones are referred to herein as a "clan". Likewise, clonotypes of phylogenic clones are referred to as phylogenic clonotypes and a set of phylogenic clonotypes may be referred to as a clan of clonotypes. In one aspect, methods of the invention comprise monitoring the frequency of a clan of clonotypes (i.e., the sum of frequencies of the constituent phylogenic clonotypes of the clan), rather than a frequency of an individual clonotype. Phylogenic clonotypes may be identified by one or more measures of relatedness to a parent clonotype. In one embodiment, phylogenic clonotypes may be grouped into the same clan by percent homology, as described more fully below. In another embodiment, phylogenic clonotypes are identified by common usage of V regions. J regions, and/or NDN regions. For example, a clan may be defined by clonotypes having common J and ND regions but different V regions; or it may be defined by clonotypes having the same V and J regions (including identical base substitutions mutations) but with different NDN regions; or it may be defined by a clonotype that has undergone one or more insertions and/or deletions of from 1-10 bases, or from 1-5 bases, or from 1-3 bases, to generate clan members. In another embodiment, members of a clan are determined as follows. Clonotypes are assigned to the same clan if they satisfy the following criteria: i) they are mapped to the same V and J reference segments, with the mappings occurring at the same relative positions in the clonotype sequence, and ii) their NDN regions are substantially identical. "Substantial" in reference to clan membership means that some small differences in the NDN region are allowed because somatic mutations may have occurred in this region. Preferably, in one embodiment, to avoid falsely calling a mutation in the NDN region, whether a base substitution is accepted as a cancer-related mutation depends directly on the size of the NDN region of the clan. For example, a method may accept a clonotype as a clan member if it has a one-base difference from clan NDN sequence(s) as a cancer-related mutation if the length of the clan NDN sequence(s) is m nucleotides or greater, e.g. 9 nucleotides or greater, otherwise it is not accepted, or if it has a two-base difference from clan NDN sequence(s) as cancer-related mutations if the length of the clan NDN sequence(s) is n nucleotides or greater, e.g. 20 nucleotides or greater, otherwise it is not accepted. In another embodiment, members of a clan are determined using the following criteria: (a) V read maps to the same V region, (b) C read maps to the same J region, (c) NDN region substantially identical (as described above), and (d) position of NDN region between V-NDN boundary and J-NDN boundary is the same (or equivalently, the number of downstream base additions to D and the number of upstream base additions to D are the same). Clonotypes of a single sample may be grouped into clans and clans from successive samples acquired at different times may be compared with one another. In particular, in one aspect of the invention, clans containing clonotypes correlated with a disease, such as a lymphoid neoplasm, are identified from clonotypes of each sample and compared with that of the immediately previous sample to determine disease status, such as, continued remission, incipient relapse, evidence of further clonal evolution, or the like.

It is expected that PCR error is concentrated in some bases that were mutated in the early cycles of PCR. Sequencing error is expected to be distributed in many bases even though it is totally random as the error is likely to have some systematic biases. It is assumed that some bases will have sequencing error at a higher rate, say 5% (5 fold the average). Given these assumptions, sequencing error becomes the dominant type of error. Distinguishing PCR errors from the occurrence of highly related clonotypes will play a role in analysis. Given the biological significance to determining that there are two or more highly related clonotypes, a conservative approach to making such calls is taken. The detection of enough of the minor clonotypes so as to be sure with high confidence (say 99.9%) that there are more than one clonotype is considered. For example of clonotypes that are present at 100 copies/1,000,000, the minor variant is detected 14 or more times for it to be designated as an independent clonotype. Similarly, for clonotypes present at 1,000 copies/1000,000 the minor variant can be detected 74 or more times to be designated as an independent clonotype. This algorithm can be enhanced by using the base quality score that is obtained with each sequenced base. If the relationship between quality score and error rate is validated above, then instead of employing the conservative 5% error rate for all bases, the quality score can be used to decide the number of reads that need to be present to call an independent clonotype. The median quality score of the specific base in all the reads can be used, or more rigorously, the likelihood of being an error can be computed given the quality score of the specific base in each read, and then the probabilities can be combined (assuming independence) to estimate the likely number of sequencing error for that base. As a result, there are different thresholds of rejecting the sequencing error hypothesis for different bases with different quality scores. For example for a clonotype present at 1,000 copies/1,000,000 the minor variant is designated independent when it is detected 22 and 74 times if the probability of error were 0.01 and 0.05, respectively.

EXAMPLE

TCRβ Repertoire Analysis: Amplification and Sequencing Strategy

In this example, TCRβ chains are analyzed. The analysis includes amplification, sequencing, and analyzing the TCRβ sequences. One primer is complementary to a common sequence in Cβ1 and Cβ2, and there are 34 V primers capable of amplifying all 48 V segments. Cβ1 or Cβ2 differ from each other at position 10 and 14 from the J/C junction. The primer for Cβ1 and Cβ2 ends at position 16 bp and has no preference for Cβ1 or Cβ2. The 34 V primers are modified from an original set of primers disclosed in Van Dongen et al, U.S. patent publication 2006/0234234, which is incorporated herein by reference. The modified primers are disclosed in Faham et al, U.S. patent publication 2010/0151471, which is also incorporated herein by reference.

The Illumina Genome Analyzer is used to sequence the amplicon produced by the above primers. A two-stage amplification is performed on messenger RNA transcripts (200), as illustrated in FIGS. 2A-2B, the first stage employing the above primers and a second stage to add common primers for bridge amplification and sequencing. As shown in FIG. 2A, a primary PCR is performed using on one side a 20 bp primer (202) whose 3' end is 16 bases from the J/C junction (204) and which is perfectly complementary to Cβ1 (203) and the two alleles of Cβ2. In the V region (206) of RNA transcripts (200), primer set (212) is provided which contains primer sequences complementary to the different V region sequences (34 in one embodiment). Primers of set (212) also contain a non-complementary tail (214) that produces amplicon (216) having primer binding site (218) specific for P7 primers (220). After a conventional multiplex PCR, amplicon (216) is formed that contains the highly diverse portion of the J(D)V region (206, 208, and 210) of the mRNA transcripts and common primer binding sites (203 and 218) for a secondary amplification to add a sample lag (221) and primers (220 and 222) for cluster formation by bridge PCR. In the secondary PCR, on the same side of the template, a primer (222 in FIG. 2B and referred to herein as "C10-17-P5") is used that has at its 3' end the sequence of the 10 bases closest to the J/C junction, followed by 17 bp with the sequence of positions 15-31 from the J/C junction, followed by the P5 sequence (224), which plays a role in cluster formation by bridge PCR in Solexa sequencing. (When the C10-17-P5 primer (222) anneals to the template generated from the first PCR, a 4 bp loop (position 11-14) is created in the template, as the primer hybridizes to the sequence of the 10 bases closest to the J/C junction and bases at positions 15-31 from the J/C junction. The looping of positions 11-14 eliminates differential amplification of templates carrying Cβ1 or Cβ2. Sequencing is then done with a primer complementary to the sequence of the 10 bases closest to the j/C junction and bases at positions 15-31 from the J/C junction (this primer is called C') C10-17-P5 primer can be HPLC purified in order to ensure that all the amplified material has intact ends that can be efficiently utilized in the cluster formation.)

In FIG. 2A, the length of the overhang on the V primers (212) is preferably 14 bp. The primary PCR is helped with a shorter overhang (214). Alternatively, for the sake of the secondary PCR, the overhang in the V primer is used in the primary PCR as long as possible because the secondary PCR is priming from this sequence. A minimum size of overhang (214) that supports an efficient secondary PCR was investigated. Two series of V primers (for two different V segments) with overhang sizes from 10 to 30 with 2 bp steps were made. Using the appropriate synthetic sequences, the first PCR was performed with each of the primers in the series and gel electrophoresis was performed to show that ill amplified.

As illustrated in FIG. 2A, the primary PCR uses 34 different V primers (212) that anneal to V region (206) of RNA templates (200) and contain a common 14 bp overhang on the 5' tail. The 14 bp is the partial sequence of one of the Illumina sequencing primers (termed the Read 2 primer). The secondary amplification primer (220) on the same side includes P7 sequence, a tag (221), and Read 2 primer sequence (223) (this primer is called Read2_tagX_P7). The P7 sequence is used for cluster formation. Read 2 primer and its complement are used for sequencing the V segment and the tag respectively. A set of 96 of these primers with tags numbered 1 through 96 are created (see below). These primers are HPLC purified in order to ensure that all the amplified material has intact ends that can be efficiently utilized in the cluster formation.

As mentioned above, the second stage primer. C-10-17-P5 (222. FIG. 2B) has interrupted homology to the template generated in the first stage PCR. The efficiency of amplification using this primer has been validated. An alternative primer to C-10-17-P5, termed CsegP5, has perfect homology to the first stage C primer and a 5' tail carrying P5. The efficiency of using C-10-17-P5 and CsegP5 in amplifying first stage PCR templates was compared by performing real time PCR. In several replicates, it was found that PCR using the C-10-17-P5 primer had little or no difference in efficiency compared with PCR using the CsegP5 primer.

Amplicon (300) resulting from the 2-stage amplification illustrated in FIGS. 2A-2B has the structure typically used with the Illumina sequencer as shown in FIG. 3A. Two primers that anneal to the outmost part of the molecule, Illumina primers P5 and P7 are used for solid phase amplification of the molecule (cluster formation). Three sequence reads are done per molecule. The first read of 100 bp is done with the C' primer, which has a melting temperature that is appropriate for the Illumina sequencing process. The second read is 6 bp long only and is solely for the purpose of identifying the sample tag. It is generated using a tag primer provided by the manufacturer (Illumina). The final read is the Read 2 primer, also provided by the manufacturer (Illumina). Using this primer, a 100 bp read in the V segment is generated starting with the 1st PCR V primer sequence.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

DEFINITIONS

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular immunology, $6^{th}$ edition (Saunders, 2007).

"Aligning" means a method of comparing a test sequence, such as a sequence read, to one or more reference sequences to determine which reference sequence or which portion of a reference sequence is closest based on some sequence distance measure. An exemplary method of aligning nucleotide sequences is the Smith Waterman algorithm. Distance measures may include Hamming distance, Levenshtein distance, or the like. Distance measures may include a component related to the quality values of nucleotides of the sequences being compared.

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155(1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Clonality" as used herein means a measure of the degree to which the distribution of clonotype abundances among clonotypes of a repertoire is skewed to a single or a few clonotypes. Roughly, clonality is an inverse measure of clonotype diversity. Many measures or statistics are available from ecology describing species-abundance relationships that may be used for clonality measures in accordance with the invention, e.g. Chapters 17 & 18, in Pielou, An Introduction to Mathematical Ecology, (Wiley-Interscience, 1969). In one aspect, a clonality measure used with the invention is a function of a clonotype profile (that is, the number of distinct clonotypes detected and their abundances), so that after a clonotype profile is measured, clonality may be computed from it to give a single number. One clonality measure is Simpson's measure, which is simply the probability that two randomly drawn clonotypes will be the same. Other clonality measures include information-based measures and McIntosh's diversity index, disclosed in Pielou (cited above).

"Clonotype" means a recombined nucleotide sequence of a T cell or B cell encoding a T cell receptor (TCR) or B cell receptor (BCR), or a portion thereof. In one aspect, a collection of all the distinct clonotypes of a population of lymphocytes of an individual is a repertoire of such population, e.g. Arstila et al, Science, 286: 958-961 (1999); Yassai et al, Immunogenetics, 61: 493-502 (2009); Kedzierska et al, Mol. Immunol., 45(3): 607-618 (2008); and the like. As used herein, "clonotype profile," or "repertoire profile," is a tabulation of clonotypes of a sample of T cells and/or B cells (such as a peripheral blood sample containing such cells) that includes substantially all of the repertoire's clonotypes and their relative abundances. "Clonotype profile," "repertoire profile," and "repertoire" are used herein interchangeably. (That is, the term "repertoire," as discussed more fully below, means a repertoire measured from a sample of lymphocytes). In one aspect of the invention, clonotypes comprise portions of an immunoglobulin heavy chain (IgH) or a TCRβ chain. In other aspects of the invention, clonotypes may be based on other recombined molecules, such as immunoglobulin light chains or TCRα chains, or portions thereof.

"Coalescing" means treating two candidate clonotypes with sequence differences as the same by determining that such differences are due to experimental or measurement error and not due to genuine biological differences. In one aspect, a sequence of a higher frequency candidate clonotype is compared to that of a lower frequency candidate clonotype and if predetermined criteria are satisfied then the number of lower frequency candidate clonotypes is added to that of the higher frequency candidate clonotype and the lower frequency candidate clonotype is thereafter disregarded. That is, the read counts associated with the lower frequency candidate clonotype are added to those of the higher frequency candidate clonotype.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

"Data structure" means an organization of information, usually in a computer or memory device, for better algorithm efficiency. Exemplary data structures include queues, stacks, linked lists, heaps, hash tables, arrays, trees, and the like. Data structures may have substructures that correspond to units of information or to subsets of related information. For example, arrays have rows and columns of entries; trees have nodes, branches, subtrees, and leaves; or the like. In one aspect, a data structure used herein is a sequence tree, an array or a hash table.

"Lymphoid neoplasm" means an abnormal proliferation of lymphocytes that may be malignant or non-malignant. A lymphoid cancer is a malignant lymphoid neoplasm. Lymphoid neoplasms are the result of, or are associated with, lymphoproliferative disorders, including but not limited to, follicular lymphoma, chronic lymphocytic leukemia (CLL), acute lymphocytic leukemia (ALL), hairy cell leukemia, lymphomas, multiple myeloma, post-transplant lymphoproliferative disorder, mantle cell lymphoma (MCL), diffuse large B cell lymphoma (DLBCL), T cell lymphoma, or the like; e.g. Jaffe et al, Blood, 112: 4384-4399 (2008); Swerdlow et al, WHO Classification of Tumours of Haematopoietic and Lymphoid Tissues (e. $4^{th}$) (IARC Press 2008).

"Percent homologous," "percent identical," or like terms used in reference to the comparison of a reference sequence and another sequence ("comparison sequence") mean that in an optimal alignment between the two sequences, the comparison sequence is identical to the reference sequence in a number of subunit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent identities may be determined with commercially available implementations of algorithms, such as that described by Needleman and Wunsch, J. Mol. Biol., 48: 443-453 (1970)("GAP" program of Wisconsin Sequence Analysis Package, Genetics Computer Group, Madison, Wis.), or the like. Other software packages in the art for constructing alignments and calculating percentage identity or other measures of similarity include the "BestFit" program, based on the algorithm of Smith and Waterman, Advances in Applied Mathematics, 2: 482-489 (1981) (Wisconsin Sequence Analysis Package. Genetics Computer Group. Madison, Wis.). In other words, for example, to obtain a polynucleotide having a nucleotide sequence at least 95 percent identical to a reference nucleotide sequence, up to five percent of the nucleotides in the reference sequence may be deleted or substituted with another nucleotide, or a number of nucleotides up to five percent of the total number of nucleotides in the reference sequence may be inserted into the reference sequence.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >9° C., primers annealed at a temperature in the range 50-75° C., and primers extended at a temperature in the range 72-7° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product. i.e. amplicon, is monitored as the reaction proceeds. There are many forms of real-time PCR that differ mainly in the detection chemistries used for monitoring the reaction product, e.g. Gelfand t a, U.S. Pat. No. 5,210,015 ("taqman"); Wittwer et al, U.S. Pat. Nos. 6,174,670 and 6,569,627 (intercalating dyes); Tyagi et al. U.S. Pat. No. 5,925,517 (molecular beacons); which patents are incorporated herein by reference. Detection chemistries for real-time PCR are reviewed in Mackay et al. Nucleic Acids Research, 30:1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or, nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco at al, Gene, 122: 3013-3020 (1992); Becker-Andre et al. Nucleic Acids Research, 17: 9437-9446 (1989); and the like.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual 2 Edition (Cold Spring Harbor Press, New York, 2003).

"Quality score" means a measure of the probability that a base assignment at a particular sequence location is correct. A variety methods are well known to those of ordinary skill for calculating quality scores for particular circumstances, such as, for bases called as a result of different sequencing chemistries, detection systems, base-calling algorithms, and so on. Generally, quality score values are monotonically related to probabilities of correct base calling. For example, a quality score, or Q, of 10 may mean that there is a 90 percent chance that a base is called correctly, a Q of 20 may mean that there is a 99 percent chance that a base is called correctly, and so on. For some sequencing platforms, particularly those using sequencing-by-synthesis chemistries, average quality scores decrease as a function of sequence read length, so that quality scores at the beginning of a sequence read are higher than those at the end of a sequence read, such declines being due to phenomena such as incomplete extensions, carry forward extensions, loss of template, loss of polymerase, capping failures, deprotection failures, and the like.

"Repertoire", or "immune repertoire", means a set of distinct recombined nucleotide sequences that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, a population of lymphocytes from which a repertoire is determined is taken from one or more tissue samples, such as one or more blood samples. A member nucleotide sequence of a repertoire is referred to herein as a "clonotype." In one aspect, clonotypes of a repertoire comprises any segment of nucleic acid common to a T cell or a B cell population which has undergone somatic recombination during the development of TCRs or BCRs, including normal or aberrant (e.g. associated with cancers) precursor molecules thereof, including, but not limited to, any of the following: an immunoglobulin heavy chain (IgH) or subsets thereof (e.g. an IgH variable region, CDR3 region, or the like), incomplete IgH molecules, an immunoglobulin light chain or subsets thereof (e.g. a variable region, CDR region, or the like), T cell receptor a chain or subsets thereof, T cell receptor β chain or subsets thereof (e.g. variable region, CDR3, V(D)J region, or the like), a CDR (including CDR1, CDR2 or CDR3, of either TCRs or BCRs, or combinations of such CDRs), V(D)J regions of either TCRs or BCRs, hypermutated regions of IgH variable regions, or the like. In one aspect, nucleic acid segments defining clonotypes of a repertoire are selected-so that their diversity (i.e. the number of distinct nucleic acid sequences in the set) is large enough so that substantially every T cell or B cell or clone thereof in an individual carries a unique nucleic acid sequence of such repertoire. That is, in accordance with the invention, a practitioner may select for defining clonotypes a particular segment or region of recombined nucleic acids that encode TCRs or BCRs that do not reflect the full diversity of a population of T cells or B cells; however, preferably, clonotypes are defined so that they do reflect the diversity of the population of T cells and/or B cells from which they are derived. That is, preferably each different clone of a sample has different clonotype. (Of course, in some applications, there will be multiple copies of one or more particular clonotypes within a profile, such as in the case of samples from leukemia or lymphoma patients). In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In one embodiment, a repertoire comprising human TCRβ chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In another embodiment, a repertoire comprising human IgH chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In a particular embodiment, a repertoire of the invention comprises a set of nucleotide sequences encoding substantially all segments of the V(D)J region of an IgH chain. In one aspect. "substantially all" as used herein means every segment having a relative abundance of 0.001 percent or higher, or in another aspect, "substantially all" as used herein means every segment having a relative abundance of 0.0001 percent or higher. In another particular embodiment, a repertoire of the invention comprises a set of nucleotide sequences that encodes substantially all segments of the V(D)J region of a TCRβ chain. In another embodiment, a repertoire of the invention comprises a set of nucleotide sequences having lengths in the range of from 25-200 nucleotides and including segments of the V, D, and J regions of a TCRβ chain. In another embodiment, a repertoire of the invention comprises a set of nucleotide sequences having lengths in the range of from 25-200 nucleotides and including segments of the V, D, and J regions of an IgH chain. In another embodiment, a repertoire of the invention comprises a number of distinct nucleotide sequences that is substantially equivalent to the number of lymphocytes expressing a distinct IgH chain. In another embodiment, a repertoire of the invention comprises a number of distinct nucleotide sequences that is substantially equivalent to the number of lymphocytes expressing a distinct TCRβ chain. In still another embodiment, "substantially equivalent" means that with ninety-nine percent probability a repertoire of nucleotide sequences will include a nucleotide sequence encoding an IgH or TCRβ or portion thereof carried or expressed by every lymphocyte of a population of an individual at a frequency of 0.001 percent or greater. In still another embodiment, "substantially equivalent" means that with ninety-nine percent probability a repertoire of nucleotide sequences will include a nucleotide sequence encoding an IgH or TCRβ or portion thereof carried or expressed by every lymphocyte present at a frequency of 0.0001 percent or greater. The sets of clonotypes described in the foregoing two sentences are sometimes referred to herein as representing the "full repertoire" of IgH and/or TCRβ sequences. As mentioned above, when measuring or generating a clonotype profile (or repertoire profile), a sufficiently large sample of lymphocytes is obtained so that such profile provides a reasonably accurate representation of a repertoire for a particular application. In one aspect, samples comprising from $10^5$ to $10^7$ lymphocytes are employed, especially when obtained from peripheral blood samples of from 1-10 mL.

"Sequence read" means a sequence of nucleotides determined from a sequence or stream of data generated by a sequencing technique, which determination is made, for example, by means of base-calling software associated with the technique. e.g. base-calling software from a commercial provider of a DNA sequencing platform. A sequence read usually includes quality scores for each nucleotide in the sequence. Typically, sequence reads are made by extending a primer along a template nucleic acid, e.g. with a DNA polymerase or a DNA ligase. Data is generated by recording signals, such as optical, chemical (e.g. pH change), or electrical signals, associated with such extension. Such initial data is converted into a sequence read.

"Sequence tree" means a tree data structure for representing nucleotide sequences. In one aspect, a tree data structure of the invention is a rooted directed tree comprising nodes and edges that do not include cycles, or cyclical pathways. Edges from nodes of tree data structures of the invention are usually ordered. Nodes and/or edges are structures that may contain, or be associated with, a value. Each node in a tree has zero or more child nodes, which by convention are shown below it in the tree. A node that has a child is called the child's parent node. A node has at most one parent. Nodes that do not have any children are called leaf nodes. The topmost node in a tree is called the root node. Being the topmost node, the root node will not have parents. It is the node at which operations on the tree commonly begin (although some algorithms begin with the leaf nodes and work up ending at the root). All other nodes can be reached from it by following edges or links.

What is claimed is:

1. A method of determining clonotypes of an immune repertoire, said method comprising the steps:

obtaining from a subject a sample comprising T-cells and/or B-cells;

spatially isolating on a solid surface individual molecules of recombined nucleic acids encoding T cell receptor molecules or immunoglobulin molecules from said T-cells and/or B-cells of said sample;

sequencing by synthesis using reversibly terminated labeled nucleotides said spatially isolated individual molecules of recombined nucleic acids to generate a set of sequence reads, said molecules of recombined nucleic acids each having a V region, an NDN region and a J region, wherein clonotypes are formed from said set of sequence reads by:

(a) constructing from sequence reads encompassing at least a portion of an NDN region a sequence tree having leaves representing candidate clonotypes, each leaf and its corresponding candidate clonotype having a frequency;

(b) coalescing with a highest frequency candidate clonotype any lesser frequency candidate clonotype whenever a lesser frequency of said lesser frequency candidate clonotype is below a predetermined frequency value and a sequence difference therebetween is below a predetermined difference value to form a clonotype having a sequence of said highest frequency candidate clonotype and having associated sequence reads summed from said highest frequency candidate clonotype and said lesser frequency candidate clonotype;

(c) removing leaves corresponding to said coalesced candidate clonotypes from said sequence tree; and (d) repeating steps (b) and (c) until a highest frequency of a lesser frequency candidate clonotype is below a predetermined stopping value, thereby determining clonotypes from said sample.

2. The method of claim 1 wherein said predetermined difference value is a predetermined Hamming distance.

3. The method of claim 1 wherein said predetermined difference value of said sequence difference is a non-increasing function of how many times said steps (b) and (c) have been repeated.

4. The method of claim 1 wherein said predetermined difference value of said sequence difference is a non-increasing function of said frequency of said highest frequency candidate clonotype.

5. The method of claim 1 wherein said sequence difference between said highest frequency candidate clonotype and said lesser frequency candidate clonotype comprises differences at one or more nucleotide locations, and wherein said highest frequency candidate clonotype is coalesced with any said lesser frequency candidate clonotype to form said clonotype whenever a function depending on frequencies of said highest frequency candidate clonotype, said lesser frequency candidate clonotype, said sequence difference and quality scores of said one or more nucleotide locations is greater than a predetermined coalescence value, wherein said function (i) monotonically increases with increasing ratio of frequency of said highest frequency candidate clonotype and frequency of said lesser frequency candidate clonotype, (ii) monotonically decreases with increasing sequence difference between said highest frequency candidate clonotype and said lesser frequency candidate clonotype, and (iii) monotonically decreases with increasing quality scores of said one or more nucleotide locations.

6. The method of claim 5 wherein said function monotonically decreases with an average of quality scores of said one or more nucleotide locations.

7. The method of claim 1 further including a step of aligning said sequence reads encompassing portions of said V regions and portions of said J regions to V and J region references respectively to determine said V and J regions of said molecules of recombined nucleic acids.

8. The method of claim 7 wherein said step of aligning includes aligning said sequence reads encompassing said portions of said V regions to a sequence tree of said V region references and aligning said sequence reads encompassing said portions of said J regions to a sequence tree of said J region references.

9. The method of claim 1 wherein for each of said molecules at least one sequence read encompasses said NDN region and portions of adjoining V and J regions thereof.

10. The method of claim 1 further including prior to said step of coalescing a step of identifying for each said highest frequency candidate clonotype selected all said lesser frequency candidate clonotype having a sequence difference therebetween less than said predetermined difference value.

11. The method of claim 10 wherein said step of identifying includes comparing said highest frequency candidate clonotype selected with every lesser frequency candidate clonotype using dynamic programming.

12. The method of claim 11 wherein said comparing is carried out by banded dynamic programming.

13. The method of claim 1 wherein said sequence difference includes differences due to nucleotide substitutions, insertions and deletions.

14. The method of claim 1 wherein said set of sequence reads comprises at least 1000 sequence reads of at least 30 nucleotides in length.

15. The method of claim 1 wherein said predetermined stopping value is a frequency corresponding to a singleton lesser frequency candidate clonotype or a frequency corresponding to a single lymphocyte.

16. A method of determining clonotypes of an immune repertoire, said method comprising the steps:

obtaining from a subject a sample comprising T-cells and/or B-cells;

spatially isolating on a solid surface individual molecules of recombined nucleic acids encoding T cell receptor molecules or immunoglobulin molecules from said T-cells and/or B-cells;

sequencing by synthesis using reversibly terminated labeled nucleotides said spatially isolated individual molecules of recombined nucleic acids to generate a set of sequence reads, said molecules of recombined nucleic acids each having portions of a V region, an NDN region and a J region wherein clonotypes are formed from said set of sequence reads by:

(a) constructing from sequence reads encompassing portions of NDN regions a sequence tree having leaves representing candidate clonotypes, each leaf and its corresponding candidate clonotype having a frequency;

(b) selecting a highest frequency candidate clonotype and identifying all lesser frequency candidate clonotype having a sequence difference therewith less than a predetermined difference value to form a coalescence subset;

(c) coalescing with said highest frequency candidate clonotype any lesser frequency candidate clonotype in said coalescence subset whenever a lesser frequency of said lesser frequency candidate clonotype is below a predetermined frequency value to form a clonotype having a sequence of said highest frequency candidate clonotype and having associated sequence reads summed from said highest frequency candidate clonotype and said lesser frequency candidate clonotype;

(d) removing leaves corresponding to said coalesced candidate clonotypes from said sequence tree; and (e) repeating steps (b) through (d) until clonotypes have been formed from all non-singleton lesser frequency candidate clonotypes, thereby determining clonotypes from said sample.

17. The method of claim 16 wherein said predetermined difference value is a predetermined Hamming distance.

18. The method of claim 16 wherein said predetermined difference value of said sequence difference is a non-increasing function of said frequency of said highest frequency candidate clonotype.

19. The method of claim 16 wherein said sequence difference between said highest frequency candidate clonotype and said lesser frequency candidate clonotype comprises differences at one or more nucleotide locations, and wherein said highest frequency candidate clonotype is coalesced with any said lesser frequency candidate clonotype to form said clonotype whenever a function depending on frequencies of said highest frequency candidate clonotype, said lesser frequency candidate clonotype, said sequence difference and quality scores of said one or more nucleotide locations is greater than a predetermined coalescence value, wherein said function (i) monotonically increases with increasing ratio of frequency of said highest frequency candidate clonotype and frequency of said lesser frequency candidate clonotype, (ii) monotonically decreases with increasing sequence difference between said highest frequency candidate clonotype and said lesser frequency candidate clonotype, and (iii) monotonically decreases with increasing quality scores of said one or more nucleotide locations.

20. The method of claim 19 wherein said function monotonically decreases with an average of quality scores of said one or more nucleotide locations.

21. The method of claim 16 wherein for each of said molecules at least one sequence read encompasses said NDN region and portions of adjoining V and J regions thereof.

22. A method of generating a clonotype profile from an individual, said method comprising the steps of:
   (a) spatially isolating on a solid surface individual molecules of recombined nucleic acids from a sample containing T-cells and/or B-cells of said individual, wherein said recombined nucleic acids encode T cell receptor molecules or immunoglobulin molecules;
   (b) sequencing by synthesis using reversibly terminated labeled nucleotides said spatially isolated individual molecules to produce a plurality of sequence reads each having portions of a V region, an NDN region and a J region and forming from sequence reads encompassing an NDN region a sequence tree having leaves representing candidate clonotypes, each leaf and its corresponding candidate clonotype having a frequency;
   (c) coalescing with a highest frequency candidate clonotype any lesser frequency candidate clonotype whenever a lesser frequency of said lesser frequency candidate clonotype is below a predetermined frequency value and a sequence difference therebetween is below a predetermined difference value to form a clonotype having a sequence of said highest frequency candidate clonotype and having associated sequence reads summed from said highest frequency candidate clonotype and said lesser frequency candidate clonotype and wherein such coalesced lesser frequency candidate clonotype is thereafter disregarded; and
   (d) repeating step (c) until clonotypes have been formed from all non-singleton lesser frequency candidate clonotypes, thereby generating said clonotype profile.

23. The method of claim 22 wherein said predetermined difference value is a predetermined Hamming distance.

24. The method of claim 22 wherein said predetermined difference value of said sequence difference is a non-increasing function of said frequency of said highest frequency candidate clonotype.

25. The method of claim 22 wherein said sequence difference between said highest frequency candidate clonotype and said lesser frequency candidate clonotype comprises differences at one or more nucleotide locations, and wherein said highest frequency candidate clonotype is coalesced with any said lesser frequency candidate clonotype to form said clonotype whenever a function depending on frequencies of said highest frequency candidate clonotype, said lesser frequency candidate clonotype, said sequence difference and quality scores of said one or more nucleotide locations is greater than a predetermined coalescence value, wherein said function (i) monotonically increases with increasing ratio of frequency of said highest frequency candidate clonotype and frequency of said lesser frequency candidate clonotype, (ii) monotonically decreases with increasing sequence difference between said highest frequency candidate clonotype and said lesser frequency candidate clonotype, and (iii) monotonically decreases with increasing quality scores of said one or more nucleotide locations.

26. The method of claim 25 wherein said function monotonically decreases with an average of quality scores of said one or more nucleotide locations.

27. The method of claim 22 further including a step of aligning said sequence reads encompassing portions of said V regions and portions of said J regions to V and J region references respectively to determine said V and J regions of said recombined nucleic acids.

28. The method of claim 27 wherein said step of aligning includes aligning said sequence reads encompassing said portions of said V regions to a sequence tree of said V region references and aligning said sequence reads encompassing said portions of said J regions to a sequence tree of said J region references.

29. The method of claim 22 wherein for each of said molecules at least one sequence read encompasses said NDN region and portions of adjoining V and J regions thereof.

30. The method of claim 1 further comprising a step of amplifying said molecules of recombined nucleic acids from said sample.

31. The method of claim 30 wherein said sample comprises at least 10,000 T cells and wherein said recombined nucleic acids encode a TCRβ chain or a portion thereof.

32. The method of claim 30 wherein said sample comprises at least 10,000 B cells and wherein said recombined nucleic acids encode an IgH chain or a portion thereof.

33. The method of claim 30 wherein said sequence reads each have a length in a range of from 20 to 400 nucleotides.

34. The method of claim 30 wherein said sample is a blood sample.

35. The method of claim 30 wherein said sequence reads each have a length less than 300 bp.

36. The method of claim 16 further comprising a step of amplifying said molecules of recombined nucleic acids from said sample.

37. The method of claim 16 wherein said sample comprises at least 10,000 T cells and wherein said recombined nucleic acids encode a TCRβ chain or a portion thereof.

38. The method of claim 16 wherein said sample comprises at least 10,000 B cells and wherein said recombined nucleic acids encode an IgH chain or a portion thereof.

39. The method of claim 16 wherein said sample is a blood sample.

40. The method of claim 16 wherein said sequence reads each have a length less than 300 bp.

41. The method of claim 22 further comprising a step of amplifying said molecules of recombined nucleic acids from said sample.

42. The method of claim 22 wherein said sample comprises at least 10,000 T cells and wherein said recombined nucleic acids encode a TCRβ chain or a portion thereof.

43. The method of claim 22 wherein said sample comprises at least 10,000 B cells and wherein said recombined nucleic acids encode an IgH chain or a portion thereof.

44. The method of claim 22 wherein said sample is a blood sample.

45. The method of claim 22 wherein said sequence reads each have a length less than 300 bp.

* * * * *